(12) United States Patent
MacKinnon et al.

(10) Patent No.: US 8,405,044 B2
(45) Date of Patent: Mar. 26, 2013

(54) ACHROMATICALLY BENDING A BEAM OF CHARGED PARTICLES BY ABOUT NINETY DEGREES

(75) Inventors: Barry A. MacKinnon, Sunnyvale, CA (US); Roger H. Miller, Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 57 days.

(21) Appl. No.: 13/183,943

(22) Filed: Jul. 15, 2011

(65) Prior Publication Data
US 2013/0015364 A1 Jan. 17, 2013

(51) Int. Cl.
*G21D 1/00* (2006.01)
(52) U.S. Cl. ......... 250/396 ML; 250/396 R; 250/492.3; 313/361.1; 315/501; 315/507; 376/105
(58) Field of Classification Search .............. 250/396 R, 250/396 ML, 492.3; 313/361.1; 315/501, 315/507; 376/105; 976/DIG. 434
See application file for complete search history.

(56) References Cited

U.S. PATENT DOCUMENTS

| 3,202,817 | A | | 8/1965 | Belbeoch |
| 3,405,363 | A | * | 10/1968 | Brown ........................ 313/361.1 |
| 3,867,635 | A | | 2/1975 | Brown et al. |
| 4,191,887 | A | * | 3/1980 | Brown .................... 250/396 ML |
| 4,362,945 | A | | 12/1982 | Riecke |
| 5,483,129 | A | * | 1/1996 | Yamamoto ..................... 315/503 |
| 6,476,403 | B1 | * | 11/2002 | Dolinskii et al. ........... 250/492.3 |
| 6,635,882 | B1 | | 10/2003 | Pavlovic et al. |
| 6,737,655 | B1 | | 5/2004 | Douglas et al. |
| 8,173,981 | B2 | * | 5/2012 | Trbojevic ................... 250/493.1 |
| 2004/0113099 | A1 | * | 6/2004 | Eickhoff et al. ........... 250/492.3 |
| 2010/0038552 | A1 | * | 2/2010 | Trbojevic ............... 250/396 ML |
| 2010/0230620 | A1 | | 9/2010 | Tsoupas et al. |
| 2010/0243879 | A1 | | 9/2010 | Huang et al. |
| 2012/0209052 | A1 | * | 8/2012 | Balakin ............................. 600/9 |

FOREIGN PATENT DOCUMENTS

WO WO 2009/142547 A2 11/2009

OTHER PUBLICATIONS

Fischer et al., "SLC arc transport system—magnet design and construction," Poster paper presented at the 1985 Particle Accelerator Conference, Vancouver, B.C., Canada, May 13-16, 1985, SLAC-PUB-3612, 3 pages (Mar. 1985).

Servranckx et al., "Circular machine design techniques and tools," Report presented at the second international conference on Charged Optics, Albuquerque, New Mexico, May 19-23, 1986, SLAC-PUB-3942, 29 pages (Apr. 1986).

Bley et al., "A Dedication Synchrotron Light source for Micromechanics," Proceedings of EPAC 1992, Berlin, Germany, 1690-1692 (1992).

Einfeld et al., "Lattice and Dynamical Behaviour of the Light Source ANKA," Proceedings of EPAC 1996 Sitges, Spain, 641-643 (1996).

(Continued)

*Primary Examiner* — Michael Logie
(74) *Attorney, Agent, or Firm* — Lowenstein Sandler LLP

(57) ABSTRACT

Embodiments of the invention provide systems and methods for achromatically bending beam of charged particles by about 90° during radiation treatment. A system may include first, second, third, and fourth bending magnets serially arranged along the particle beam path. The first and fourth bending magnets are configured to generate a positive field gradient that defocuses the particle beam in the bend plane. The second and third bending magnets are configured to generate a negative field gradient that focuses the particle beam in the bend plane. The first, second, third, and fourth bending magnets collectively bend the particle beam by about 90°, e.g., by about 22.5° each.

20 Claims, 17 Drawing Sheets

OTHER PUBLICATIONS

Machida, S., "Beam Transport Line with a Scaling Type FFAG Magnet," Proceedings of PAC09 Vancouver, BC, Canada, 4360-4362 (2010).

Pasini et al., "An Isopath Achromatic Bending Section for Multi-Charge Ion Beam Transport at ISAC-II," Proceedings of EPAC 2002, Paris, France, 1175-1177 (2002).

* cited by examiner

Full Emittance Particle Beam With Finite Energy Spread, Bend Plane

Full Emittance Particle Beam With Finite Energy Spread, Non-Bend Plane

Zero Emittance Particle Beam With Finite Energy Spread, Bend Plane

Full Emittance Monochromatic Particle Beam, Bend Plane

US 8,405,044 B2

ACHROMATICALLY BENDING A BEAM OF CHARGED PARTICLES BY ABOUT NINETY DEGREES

FIELD

This application relates to systems and methods for achromatically bending a beam of charged particles by about 90° during radiation treatment.

BACKGROUND

External beam radiation therapy is one of the available non-invasive methods to treat a pathological anatomy (e.g., tumor, lesion, vascular malformation, nerve disorder, etc.). In one type of external beam radiation therapy, an external radiation source directs a sequence of x-ray beams at a target volume, e.g., a tumor, from multiple angles, with the patient positioned so the target volume is at the center of rotation (isocenter) of the beam. As the angle of the radiation source changes, every beam passes through the target volume, but passes through a different area of healthy tissue on its way to and from the target volume.

Image-guided radiation therapy (IGRT) systems include gantry-based systems and robotic-based systems. In gantry-based systems, the radiation source, e.g., a linear accelerator (LINAC), is mounted on a gantry that moves the source around a center of rotation (isocenter) in a single plane. The radiation source may be rigidly attached to the gantry or attached by a gimbaled mechanism. Each time a radiation beam is delivered to a target volume during treatment, the axis of the beam passes through the isocenter. Radiation beam delivery is, therefore, limited by the rotation range of the radiation source mounted on the gantry, the angular range of the gimbaled mechanism (if present), and by the number of degrees of freedom available on a patient positioning system. Additionally, the shape of the radiation can be modified using a multileaf collimator. Alternatively, the treatment system has the radiation source mounted on a robotic arm with at least five degrees of freedom to enable non-coplanar delivery to a target volume. One example of such a system is the CYBERKNIFE® Robotic Radiosurgery System manufactured by Accuray Incorporated. (Sunnyvale, Calif.).

One practical limitation for both gantry-based systems and robotic-based IGRT systems is space. Specifically, hospitals or other sites wishing to install such a system may have a specific room in which it is to be placed. However, the system may be too large for the room, thus requiring structural modification of the room. If the room cannot be modified within a specified budget (or at all), then it may be necessary to relocate the system; alternatively, the system's use may be entirely precluded at the site. Thus, it would be useful to reduce the size of an IGRT system. One way in which to do this is to reduce the amount of space required to generate the radiation beam (e.g., X-ray, electron, or proton beam).

One example of a prior art robot-based IGRT system 100 is illustrated in FIG. 1. System 100 includes robot-based support system 110, robot-based linear accelerator (LINAC) system 120, X-ray imaging sources 131, and detectors 132. Robot-based LINAC system 120 includes LINAC 121 and robotic arm 122. Robot-based support system 110 includes patient treatment couch 111, robotic arm 112, track 114, and column 115. Responsive to instructions from a controller (not shown), robot-based support system 110 moves robotic arm 112 in any suitable direction, e.g., along track 114 and/or column 115, so as to adjust the position and/or orientation of patient treatment couch 111 and thus appropriately position the patient before and/or during the radiation treatment, in accordance with a treatment plan. Also responsive to instructions from the controller, robot-based LINAC system 120 moves LINAC 121 to a desired position and orientation using robotic arm 122, and generates radiation of the desired type, energy, field, and dose using LINAC 121, again in accordance with the treatment plan. X-ray imaging sources 131 and detectors 132 are configured to obtain x-ray images of the patient or nearby anatomical structures responsive to instructions from the controller, e.g., at appropriate times before and during the radiation treatment. Each of x-ray imaging sources 131 is arranged at a predetermined angle relative to vertical, e.g., at 45° from vertical, such that x-ray radiation generated by that source passes through the target volume and is received by corresponding detector 132. Based on the received radiation, each of detectors 132 obtains an x-ray image of the target volume. The pair of thus-obtained images may be referred to as "stereoscopic x-ray images," and is provided from detectors 132 to the controller for use in guiding irradiation of the patient with LINAC 121.

As is familiar to those skilled in the art, LINACs are designed to accelerate charged particles along a linear pathway. Generally, a LINAC includes a charged particle source, e.g., a source of electrons, protons, or ions, and an evacuated chamber along which the particles are accelerated. Depending on the type of charged particle, the evacuated chamber may be relatively long. For example, chambers for the acceleration of electrons may be between 0.5 and 1.5 meters long. Orienting such a chamber generally perpendicularly to the patient treatment couch, as is the case for LINAC 121 illustrated in FIG. 1, may substantially increase the overall height of the system. As such, the space requirements for installing and operating the system may increase correspondingly, thus potentially presenting practical problems for installing the system at space-constrained sites.

SUMMARY

Embodiments of the invention provide systems and methods for achromatically bending a beam of charged particles by about 90°. Under one aspect of the present invention, a system for achromatically bending a particle beam by about 90° includes first, second, third, and fourth bending magnets serially arranged along a beam path of the particle beam. The first and fourth bending magnets may be configured to generate a positive field gradient that defocuses the particle beam in a bend plane. The second and third bending magnets may be configured to generate a negative field gradient that focuses the particle beam in the bend planes. The first, second, third, and fourth bending magnets collectively bend the particle beam by about 90°, and in some embodiments, they each bend the particle beam by about 22.5° about an approximate center of curvature. The first and fourth bending magnets may have substantially the same construction as one another, and the second and third bending magnets also may have substantially the same construction as one another; however, the construction of the second and third bending magnets may be different than that of the first and fourth bending magnets.

The first and fourth bending magnets each may include an iron cored, dipole electromagnet having pole faces that are symmetrically disposed about the bend plane and are inclined relative to each other and shaped so as to generate a positive field gradient. A positive field gradient is such that the magnetic induction decreases with increasing distance from the approximate center of curvature. The second and third bending magnets each may include an iron cored, dipole electromagnet and having pole faces that are symmetrically disposed about the bend plane and are inclined relative to each other and shaped so as to generate a negative field gradient. A negative field gradient is such that the magnetic induction increases with increasing distance from the approximate center of curvature. The pole faces of the first, second, third, and fourth bending magnets may be shaped such that the positive field gradient is substantially weaker than the negative field gradient. The pole faces of the first, second, third, and fourth bending magnets may each be approximately hyperbolically shaped. In some embodiments, the pole faces are shaped so as to introduce higher-order magnetic field components so as to control geometric and chromatic aberrations in the beam which may be produced by the simple linear field gradients heretofore described.

In one embodiment, a midpoint between the second and third bending magnets defines a mirror plane. The first and fourth bending magnets may be positioned substantially symmetrically across the mirror plane from one another, and the second and third bending magnets may be positioned substantially symmetrically across the mirror plane from one another.

Under another aspect of the present invention, a method for achromatically bending a particle beam by about 90° may include bending the particle beam with a first bending magnet that defocuses the particle beam in a first plane with a positive field gradient, and then bending the particle beam with a second bending magnet that focuses the particle beam in the first plane with a negative field gradient, and then bending the particle beam with a third bending magnet that focuses the particle beam in the first plane with a negative field gradient, and then bending the particle beam with a fourth bending magnet that defocuses the particle beam in the first plane with a positive field gradient, wherein the first, second, third, and fourth bending magnets collectively bend the particle beam by about 90°.

DETAILED DESCRIPTION

Embodiments of the invention provide systems and methods for achromatically bending a beam of charged particles by about 90° during radiation treatment. By "achromatic" it is meant that particles having energies that lie within a certain range, e.g., within plus or minus 10% of a central energy value, or even within plus or minus 15% of a central energy value, will all be redirected in approximately the same direction as one another and in approximately the same position as one another. Such systems and methods may significantly reduce the space requirements for installing and operating radiation treatment systems that include a linear accelerator (LINAC) for generating radiation to be used in treating a patient. Specifically, whereas prior art radiation treatment systems such as system 100 illustrated in FIG. 1 may include a long LINAC that is oriented generally perpendicularly to the patient during treatment, which can significantly increase the space requirements for installing and operating the system, the systems and methods provided herein allow a LINAC to be oriented generally parallel to the patient and achromatically bend the output of the LINAC by about 90°. Because the LINAC is generally significantly longer than it is wide, such a parallel orientation may result in significant space savings, thus allowing the radiation treatment system to be installed in smaller spaces than may otherwise be possible, and/or to allow movement of the radiation source to otherwise inaccessible locations within the treatment space. Additionally, while some existing radiation treatment systems may include systems that achromatically bend a particle beam by about 270°, such bending systems may require about three times more material than the present systems. For robot-mounted bending systems, such a weight differential may significantly impact practical implementation of the bending system.

Figure 1:
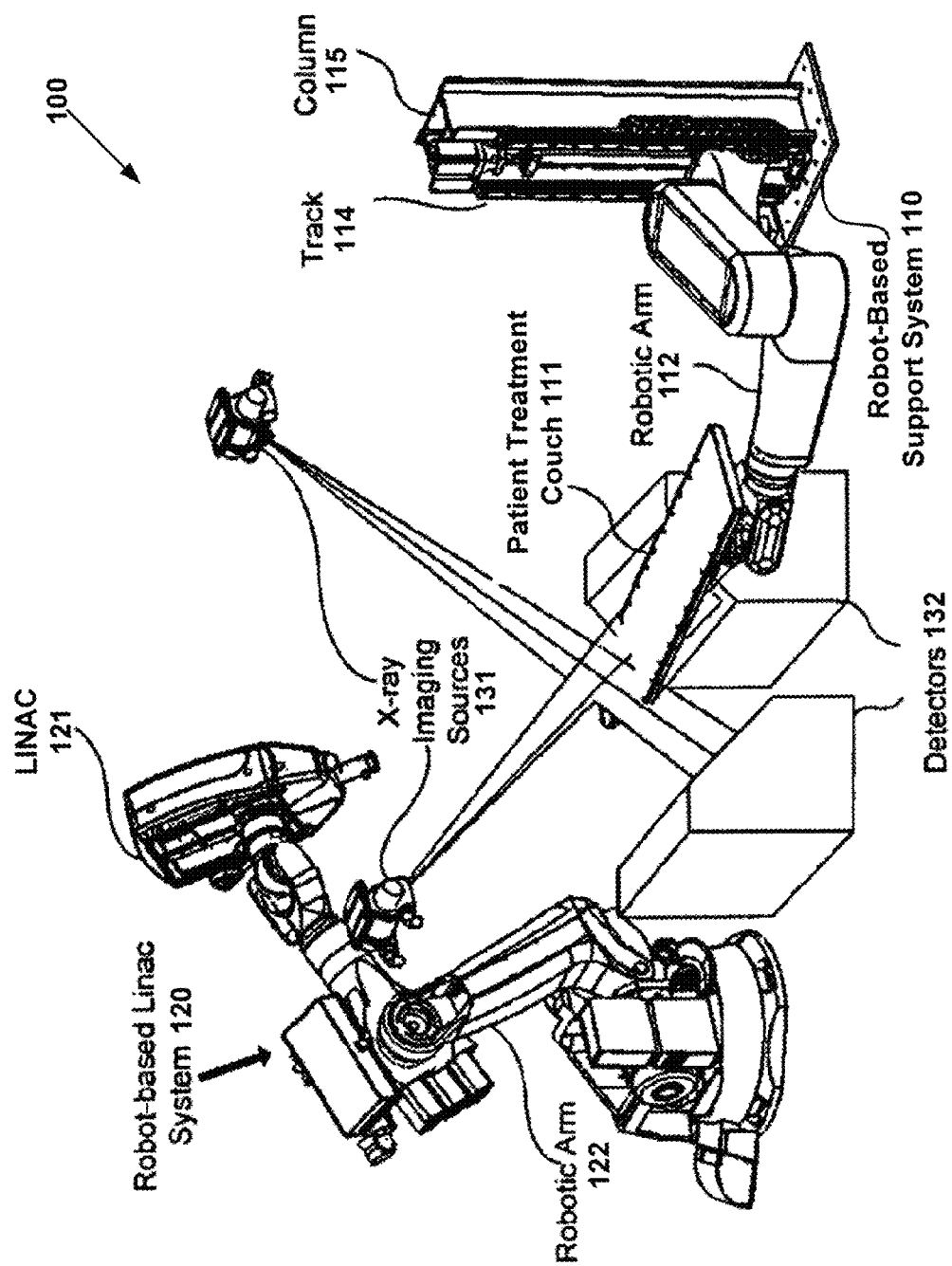
FIG. 1 schematically illustrates a perspective view of a prior art robot-based radiation treatment system.
Figure 2A:
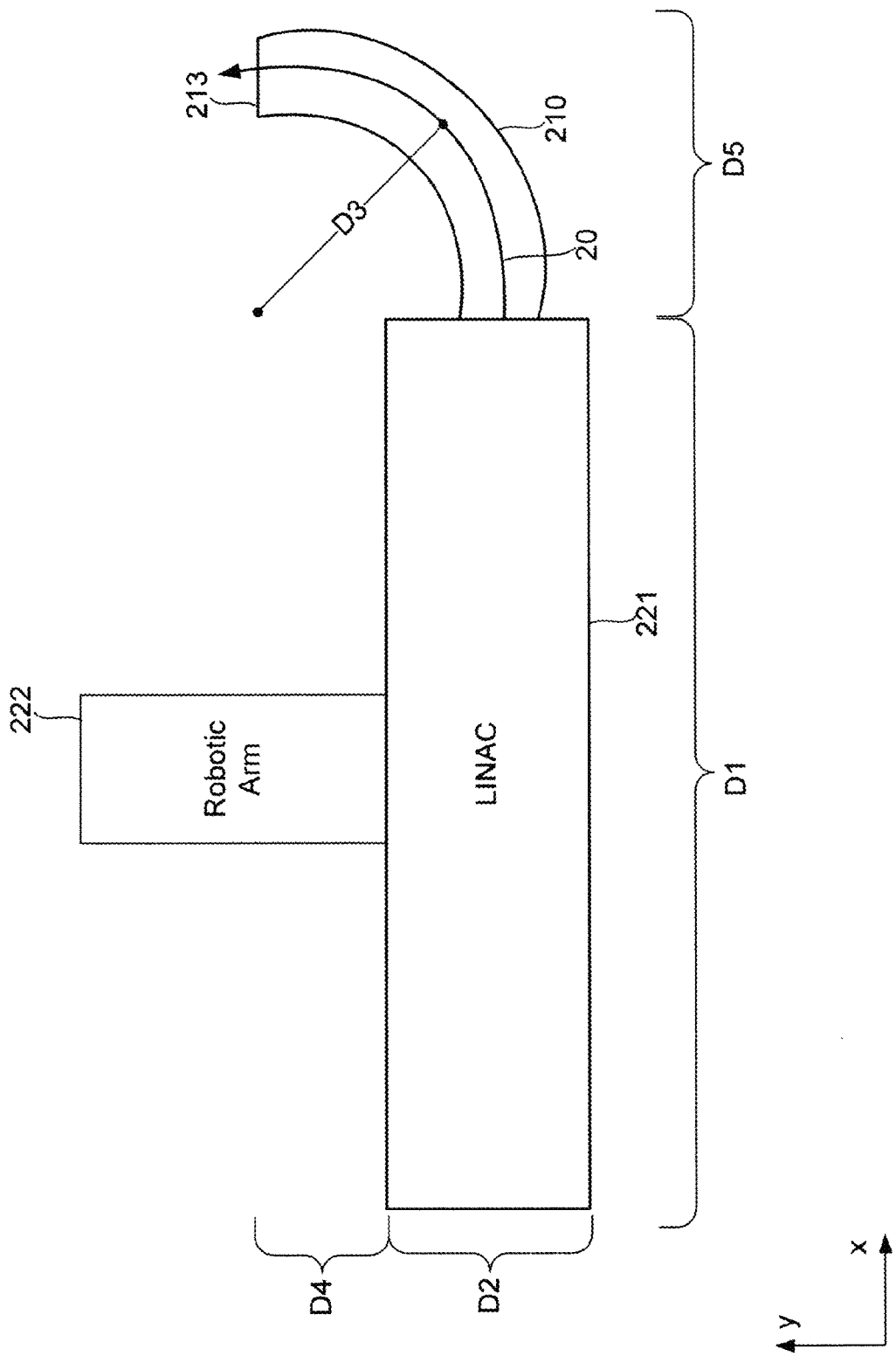
FIG. 2A schematically illustrates a plan view of a linear accelerator (LINAC) coupled to a system for achromatically bending an electron beam by about 90° during radiation treatment.

For example, FIG. 2A schematically illustrates a plan view of a LINAC 221 and beam bending system 210, according to some embodiments of the present invention. LINAC 221 is mounted on robotic arm 222, which may be similar to robotic arm 122 illustrated in FIG. 1. LINAC 221 emits a particle beam 20 in a direction that is substantially parallel to the orientation of LINAC 221. Beam bending system 210 is coupled to LINAC 221 and receives particle beam 20 from LINAC 221. Beam bending system then bends the particle beam 20 by about 90° from an axis approximately parallel to the orientation of LINAC 221, and emits the bent beam at output 213. The bent beam is thus emitted substantially perpendicular to the orientation of LINAC 221. Note that robotic arm 222 and beam bending system 210 need not necessarily be in the same plane as one another. For example, beam bending system 210 may be oriented in the x-y plane, as shown, and robotic aim may be oriented in the y-z plane, e.g., orthogonally to beam bending system 210.

As can be seen from FIG. 2A, beam bending system 210 allows LINAC 221 to be mounted so as to allow for a relatively compact arrangement. Specifically, LINAC 221 has a length D1 and a width D2 that is substantially smaller than length D1, and beam bending system 210 has a bending radius of D3. Together, LINAC 221 and beam bending system 210 have a dimension in the x-direction about equal to D1 plus D5, where D5 is the lateral dimension of the beam bending system in the x-direction. LINAC 221 and beam bending system 210 have a dimension in the y-direction about equal to D2 plus D4, where D4 is the lateral dimension of the beam bending system in the y-direction that extends past the edge of the LINAC. Usefully, the sum of D2 and D4 is significantly smaller than is D1, e.g., less than half of D1, thus resulting in significant space savings in the y-direction and potentially allowing the system to be installed at more space-constrained sites and/or to be moved to otherwise inaccessible treatment orientations.

As used herein, the terms "about" and "approximately" mean plus or minus 10% or less. For example, beam bending system 210 may bend particle beam 20 by between 81° and 99°, or between 82° and 98°, or between 83° and 97°, or between 84° and 96°, or between 85° and 95°, or between 86° and 94°, or between 87° and 93°, or between 88° and 92°, or between 89° and 91°, or between 89.5° and 90.5°, or between 89.8° and 90.2°, or between 89.9 and 90.1°, or even exactly 90°.

Figure 2B:
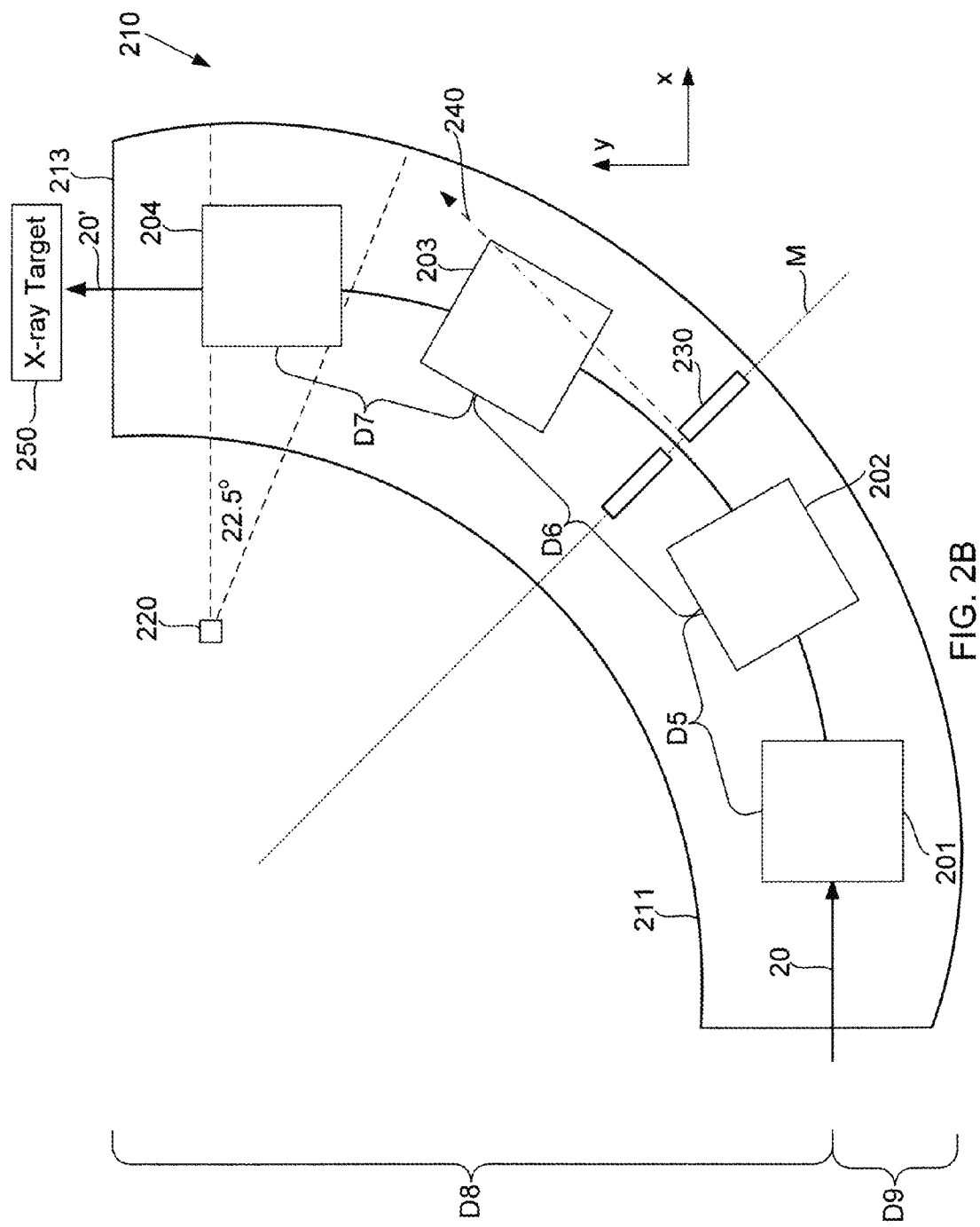
FIG. 2B schematically illustrates a more detailed plan view of the achromatic bending system of FIG. 2A.

FIG. 2B schematically illustrates one embodiment of a beam bending system 210 suitable for use with LINAC 221. Beam bending system 210 receives particle beam 20 from LINAC 221 (not shown in FIG. 2B), and bends the particle beam by about 90°, resulting in redirected beam 20'. In one embodiment, redirected beam 20' is a substantially round beam of electrons of selected energy, e.g., 6 MeV or 10 MeV, that irradiates X-ray target 250 (e.g., a tungsten target) to generate X-rays for use in radiation therapy. Other suitable charged particles may be used, with or without a target, as one of skill in the art will appreciate.

Beam bending system 210 includes first, second, third, and fourth bending magnets 201, 202, 203, and 204, respectively, that are serially arranged along the beam path of particle beam 20, and are coupled to a suitable mount 211. In the illustrated embodiment, each of the first, second, third, and fourth bending magnets 201, 202, 203, 204 each bend the particle beam by about 22.5° with respect to an approximate center of curvature, e.g., center of curvature 220 for magnet 204 (centers of curvature for the other magnets are not shown). However, it should be appreciated that each magnet may bend the particle beam by any desired angle, such that collectively the magnets 201-204 bend the beam by about 90°. For example, the first and fourth magnets 201, 204 may each bend the beam by about 15°, and the second and third magnets may each bend the beam by 30°. In embodiments where the first and fourth magnets bend the beam by about the same angle as one another, and the second and third magnets also bend the beam by about the same angle as one another, the collection of magnets may be approximately symmetrical across mirror plane M and may provide imaging at approximately 1:1 magnification of the particle beam from the first to the fourth magnet. In embodiments where the first and fourth bend the beam by a different angle as one another, and the second and third magnets bend the beam by a different angle than one another, the collection of magnets may be asymmetrical across mirror plane M and may provide imaging at a ratio of other than 1:1 magnification of the particle beam from the first to the fourth magnet. Any suitable arrangement of magnets may be used, providing any desired imaging ratio. However, it will be appreciated that imaging at an approximately 1:1 magnification ratio may be useful in some circumstances because the particle beam will have similar spatial profiles both before and after the bend.

In some embodiments, an aperture 230 may be provided between the second and third bending magnets and shaped so as to spatially filter particles that stray beyond an acceptable distance from beam path 20, e.g., particles that have energies outside of a pre-determined energy spread. As illustrated below with respect to FIGS. 3A-3B, the beam waist of the particle beam may be relatively large in the bend plane and relatively small in the non-bend plane. Where the charged particles are electrons, any electrons that strike aperture 230 may cause the emission of X-rays in the direction in which those electrons had been travelling, e.g., as denoted by the dash-dot line 240.

As illustrated in FIG. 2B, the first and second bending magnets 201, 202 are separated by a lateral center-to-center drift distance D5. The second and third bending magnets 202, 203 are separated by a lateral center-to-center drift distance D6. The third and fourth bending magnets 203, 204 are separated by a lateral center-to-center drift distance D7 that in some embodiments may be substantially the same as D5. Note that if drift distance D7 is different than drift distance D5, then the bend angle of fourth bending magnet 204 may be different from the bend angle of the first bending magnet 201 by the inverse ratio (D5/D7) to achieve achromaticity. In some embodiments, a midpoint between the second and third bending magnets 202, 203 defines a mirror plane M, across which the positions of the bending magnets may be substantially symmetrical. That is, the first and fourth bending magnets 201, 204 may be positioned substantially symmetrically from each other across mirror plane M, and the second and third bending magnets 202, 203 also may be positioned substantially symmetrically from each other across mirror plane M. Thus, in some cases, the first and fourth bending magnets may be referred to as the "outer" bending magnets, and the second and third bending magnets may be referred to as the "inner" bending magnets. The distance D8 from beam path 20 to the top edge of mount 211, plus the distance D9 from beam path 20 to the bottom edge of mount 211, defines the lateral dimensions of beam bending system 210. Note that other embodiments need not necessarily include mirror symmetry across mirror plane M, and may in some circumstances image the beam with other than 1:1 magnification.

In some embodiments, the first and fourth bending magnets 201, 204 may be substantially the same as one another, e.g., have substantially the same construction, materials, and configuration as one another. Similarly, the second and third bending magnets 202, 203 may be substantially the same as one another; however, the construction of the first and fourth bending magnets 201, 204 may be different from the construction of the second and third bending magnets 202, 203. In one embodiment, each of the first, second, third, and fourth bending magnets 201-204 are rectangular, laminated magnets, where the first and fourth magnets have pole faces that are the same as one another, and the second and third magnets have pole faces that are the same as one another but different than those of the first and fourth magnets. Such laminated magnets may be particularly useful where the field in the bend magnets may be changed relatively rapidly by a fast regulating power supply, thus facilitating achromatic bending of particle beams having central energies and/or energy spreads that differ significantly from one another. In an alternative embodiment described in greater detail below with respect to FIG. 11, trapezoidal and/or wedge-shaped magnets instead may be used to bend the particle beam.

Figure 3A:
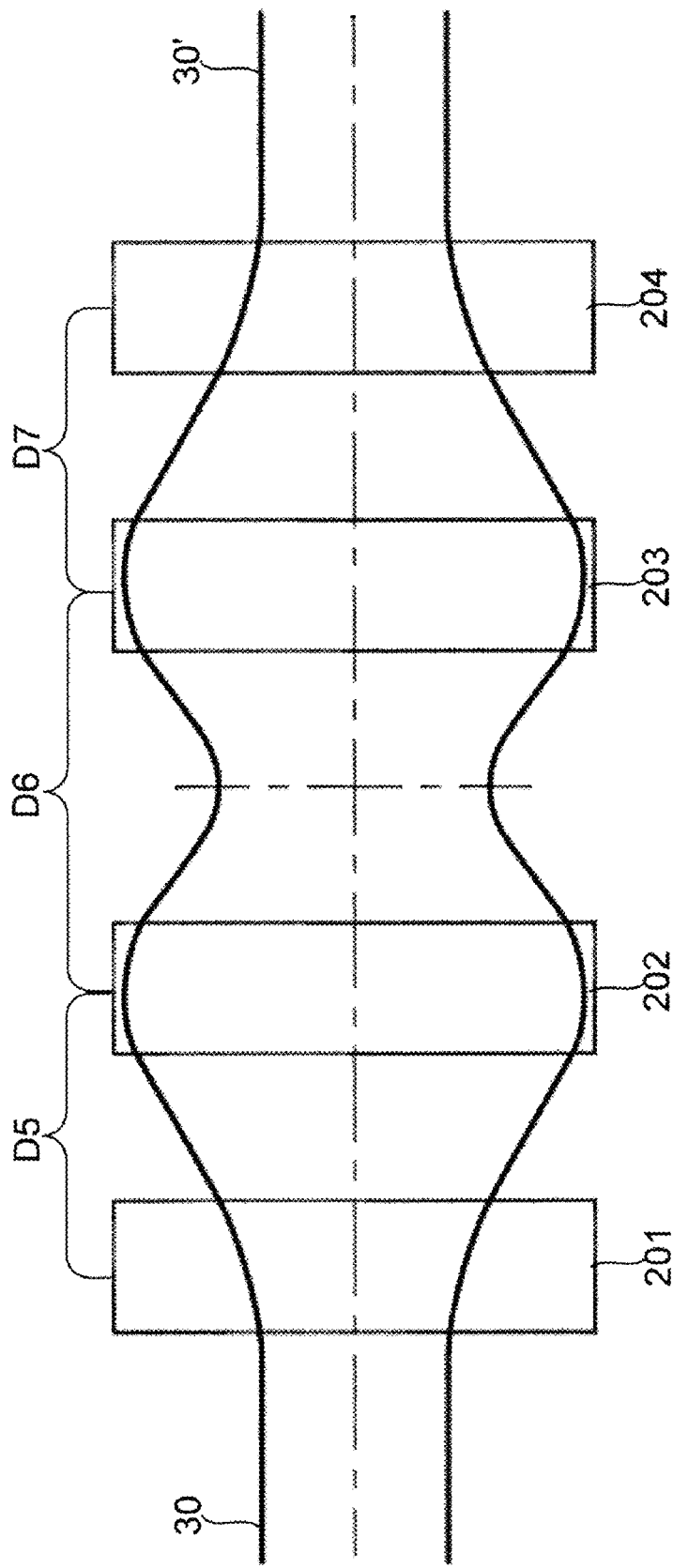
FIG. 3A schematically illustrates the bend-plane envelope of a full emittance particle beam with finite energy spread as it travels through the achromatic bending system of FIG. 2B.
Figure 3B:
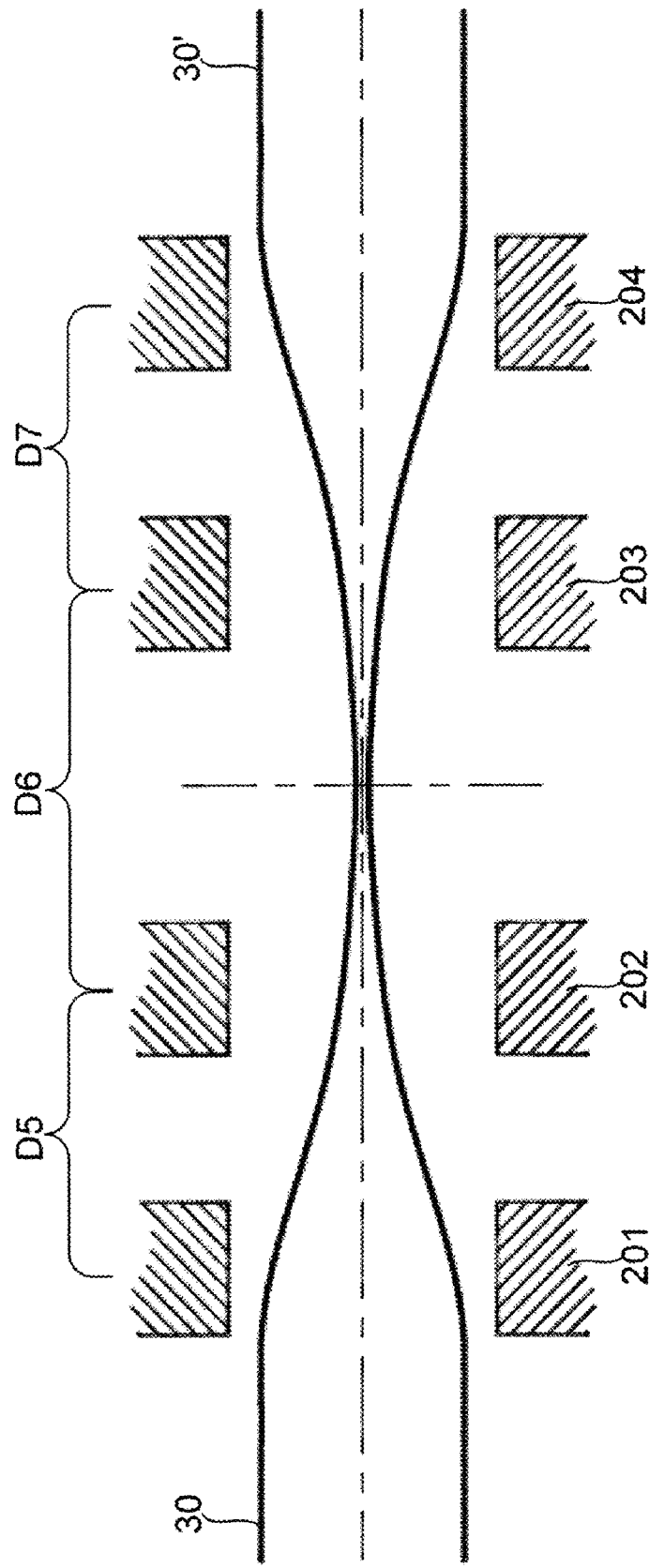
FIG. 3B schematically illustrates the non-bend plane envelope of a full emittance particle beam with finite energy spread as it travels through the achromatic bending system of FIG. 2B.

Preferably, the first, second, third, and fourth magnets 201-204 are configured so as to achromatically bend, in a bend plane, a full emittance particle beam 30 having a finite energy spread such as illustrated in FIG. 3A, in which the bending magnets are arranged along a straight line merely for simplicity of illustration and so angles and transverse positions relative to a central reference particle can be magnified. Specifically, the first and fourth bending magnets 201, 204 each may be configured to defocus the particle beam 30 in the bend plane, and have a positive field gradient. The magnitude of the field gradients of the first and fourth bending magnets 201, 204 may be substantially the same as one another. In contrast, the second and third bending magnets 202, 203 each may be configured to focus the particle beam 30 in the bend plane and have a negative field gradient. The magnitude of the field gradients of the second and third bending magnets 202, 203 may be substantially the same as one another, and substantially higher than the field gradients of the first and fourth bending magnets 201, 204, as discussed in greater detail below. The net result, illustrated in FIG. 3A, is that in the bend plane beam 30 diverges between the first and second bending magnets 201, 202, in the drift region defined by D5; converges to a waist and then diverges between the second and third bending magnets 202, 203 in the drift region defined by D6; converges between the third and fourth bending magnets 203, 204 in the drift region defined by D7; and is approximately collimated in the drift region after it passes through magnet 204, with imaging at 1:1 magnification of the beam from the first to the fourth magnet in the bend plane. FIG. 3B schematically illustrates the envelope of the same full emittance, finite energy spread particle beam 30 as shown in FIG. 3A, but instead in the non-bend plane. The first and fourth bending magnets 201, 204 each may be configured to provide imaging at 1:1 magnification of the particle beam 30 in the non-bend plane, yielding a narrow beam waist positioned approximately mid-way between the second and third bending magnets 202, 203. Note that in such a design, the use of four magnets is particularly useful for controlling the focusing and defocusing of the particles in the bend and non-bend planes.

Figure 3C:
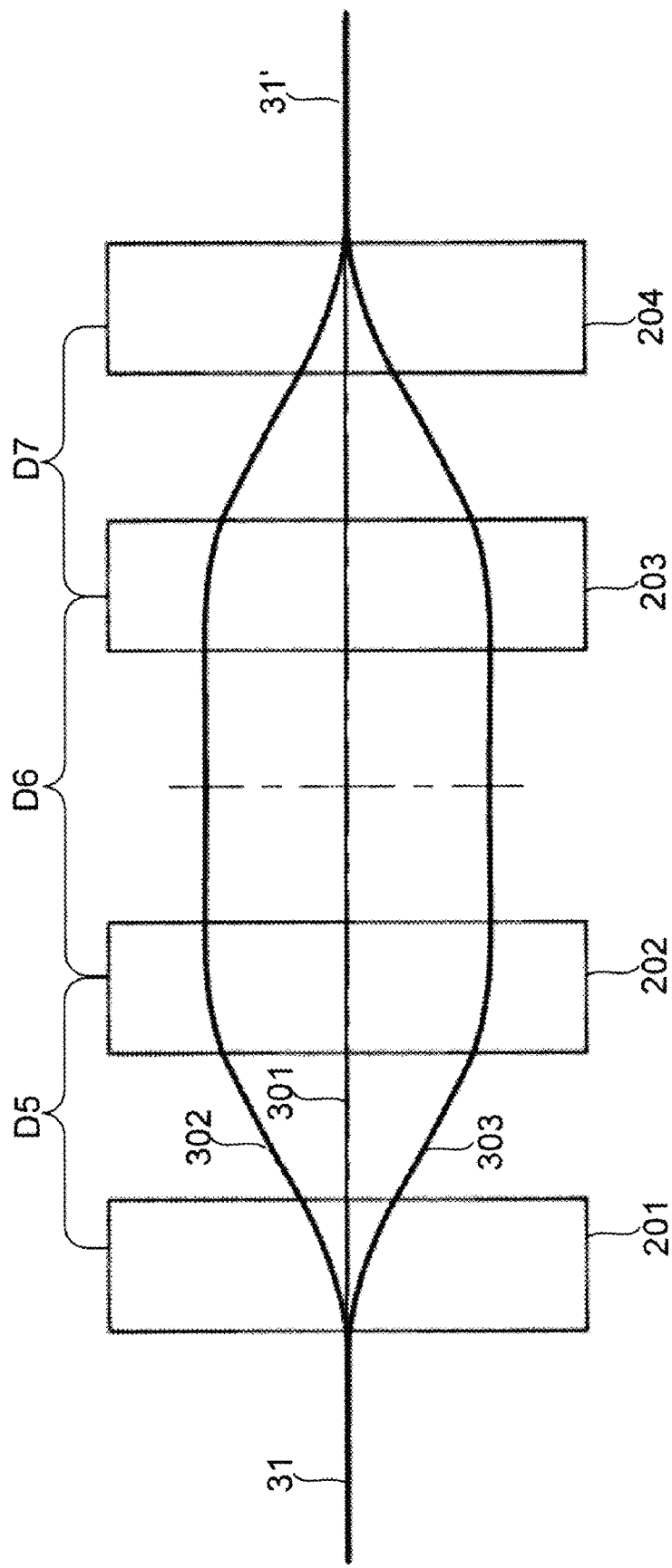
FIG. 3C schematically illustrates the bend-plane envelope of a zero emittance particle beam with finite energy spread as it travels through the achromatic bending system of FIG. 2B.

Preferably, the first, second, third, and fourth magnets 201-204 are also configured so as to achromatically bend a zero-emittance particle beam 31 having a finite energy spread, in the bend plane, in the manner illustrated in FIG. 3C, in which the bending magnets are arranged along a straight line merely for simplicity of illustration. Beam 31 includes particle 301 having the same energy as the central energy of the spread and relative to which magnified angles and transverse positions of the other particles are shown, and particles 302 and 303 having energies that are different than one another but equal and oppositely spaced from the central energy. First bending magnet 201 causes particles 302 and 303 to diverge from one another and from particle 301. Second bending magnet 202 redirects particles 302 and 303 so that their trajectories become parallel to one another and to that of particle 301. Third bending magnet 203 causes the trajectories of particles 302 and 303 to converge toward that of particle 301 at fourth bending magnet 204. Fourth bending magnet redirects particles 301, 302, and 303 such that their trajectories recombine with one another, again forming a zero emittance particle beam with finite energy spread 31'. The parallel and collinear paths of particles 301, 302, and 303 in the exit beam 31' evidence the achromaticity of the system.

Figure 3D:
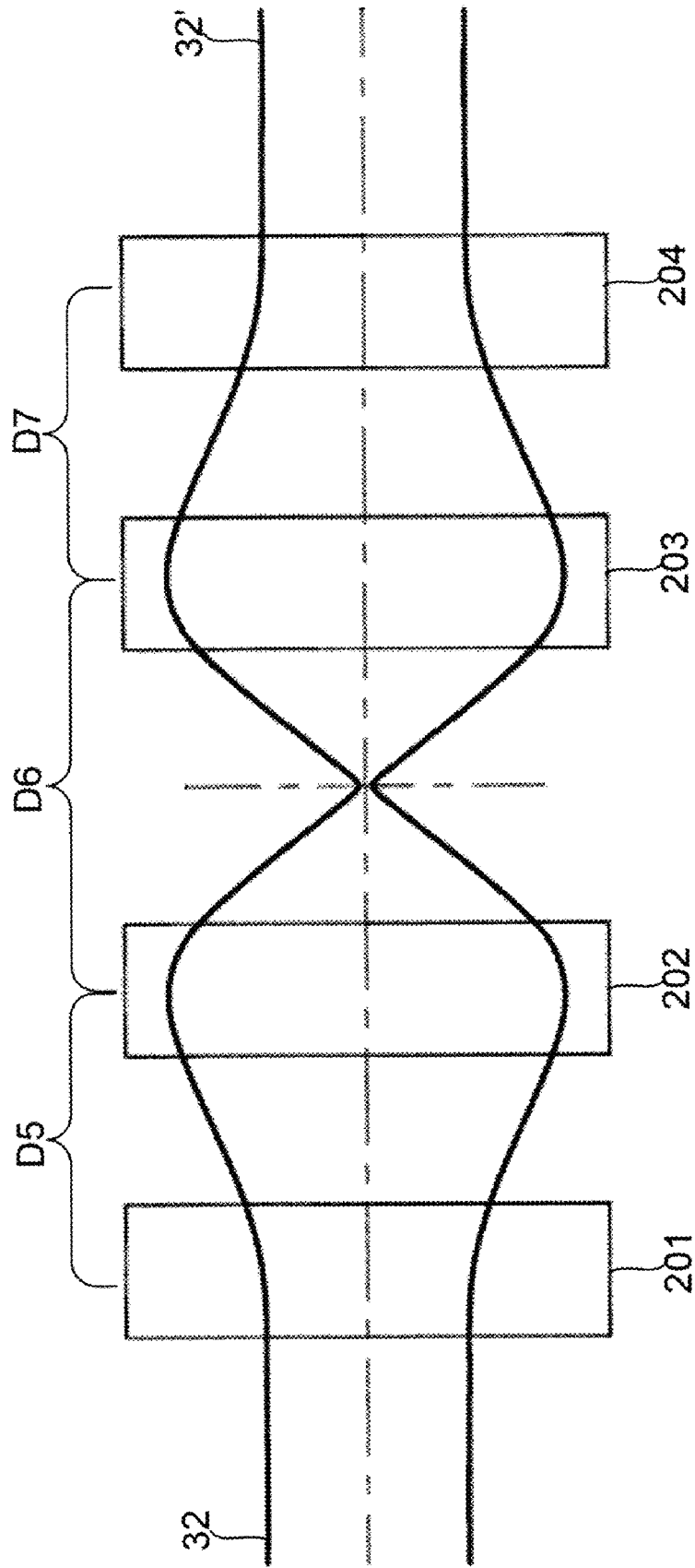
FIG. 3D schematically illustrates the bend-plane envelope of a full emittance, monochromatic particle beam as it travels through the achromatic bending system of FIG. 2B.

Preferably, the first, second, third, and fourth magnets 201-204 are also configured so as to achromatically bend a full emittance monochromatic particle beam 32 in the bend plane in the manner illustrated in FIG. 3D, in which the bending magnets are arranged along a straight line merely for simplicity of illustration. First bending magnet 201 defocuses beam 32, then second bending magnet 202 focuses beam 32 to a relatively small beam waist that appears as a crossover at the midpoint between the second and third bending magnets. Drift distance D6 is selected to achieve this condition, which also provides the system with beam imaging at 1:1 magnification from input to output in the bend plane, as compared to that which could be achieved with a three-magnet system. Third bending magnet 203 focuses beam 32, and then the fourth bending magnet 204 collimates the beam, resulting in collimated beam 32'. Preferably, the beam path illustrated in FIG. 3A is the root mean square (RMS) of the beam paths illustrated in FIGS. 3C and 3D.

Note that charged particles within the actual particle beam that is input to beam bending system 210 may have finite emittance and a finite energy spread, that is, the beam is not necessarily mono-directional and/or monochromatic. For example, particles within the particle beam may have energies that are within plus or minus 10%, or even within plus or minus 15%, of a central energy value; that is, the beam may have a 20% or even a 30% full width energy spread. Preferably, the first, second, third, and fourth bending magnets are constructed and arranged such that beam bending system 210 is substantially achromatic to first order. By "substantially achromatic to first order" it is meant that particles having energies within a specified range of energies will be bent in substantially the same direction as one another and that their position will also be substantially independent of their energies. In one embodiment, beam bending system 210 bends in substantially the same direction particles that deviate from a central energy by plus or minus 7% of a central energy value. Additionally, the magnets also may be constructed and arranged to image the beam in the both the bend and non-bend planes from the first to the fourth magnet with a magnification of one. Such beam shaping characteristics and achromaticity may be achieved, for example, by (1) selecting the field index and/or focal length of the inner (second and third) magnets so as to image the beam in the bend plane from approximately the center of the first magnet to the center of the fourth magnet (achromaticity condition); (2) selecting the field index and/or focal length of the outer (first and fourth) magnets so as to produce imaging at 1:1 magnification in the non-bend plane; and (3) selecting the drift length D6 between the inner (second and third) magnets so as to produce imaging at 1:1 magnification in the bend plane. In one embodiment, such imaging at 1:1 magnification is achieved for full emittance finite energy-spread beams, zero emittance finite energy-spread beams, as well as full emittance monochromatic beams, by constructing the system to have mirror symmetry about a mirror image plane M. Note, however, that such mirror symmetry is not required, and imaging at magnifications other than 1:1 may be provided.

System 210 illustrated in FIGS. 2A-2B may be used to deflect any suitable beam of charged particles by about 90°. It will be appreciated, however, that the specific dimensions of system 210 and configurations of bending magnets 201-204 may be adjusted based on the masses and energies of the particles in particle beam 20. For example, electrons have relatively low masses and so may be deflected over a shorter distance than protons or heavier ions. Exemplary dimensions of the system of FIGS. 2A-2B, as configured for use with electrons of energies 6 MeV or 10 MeV, are set forth below in Table 1.

TABLE 1

| Dimension | 6 MeV Electrons | 10 MeV Electrons |
| --- | --- | --- |
| D5, D7 | 25 mm | 25 mm |
| D6 | 48 mm | 48 mm |
| D8 | 154 mm | 165 mm |
| D9 | 29 mm | 30 mm |

Figure 4:
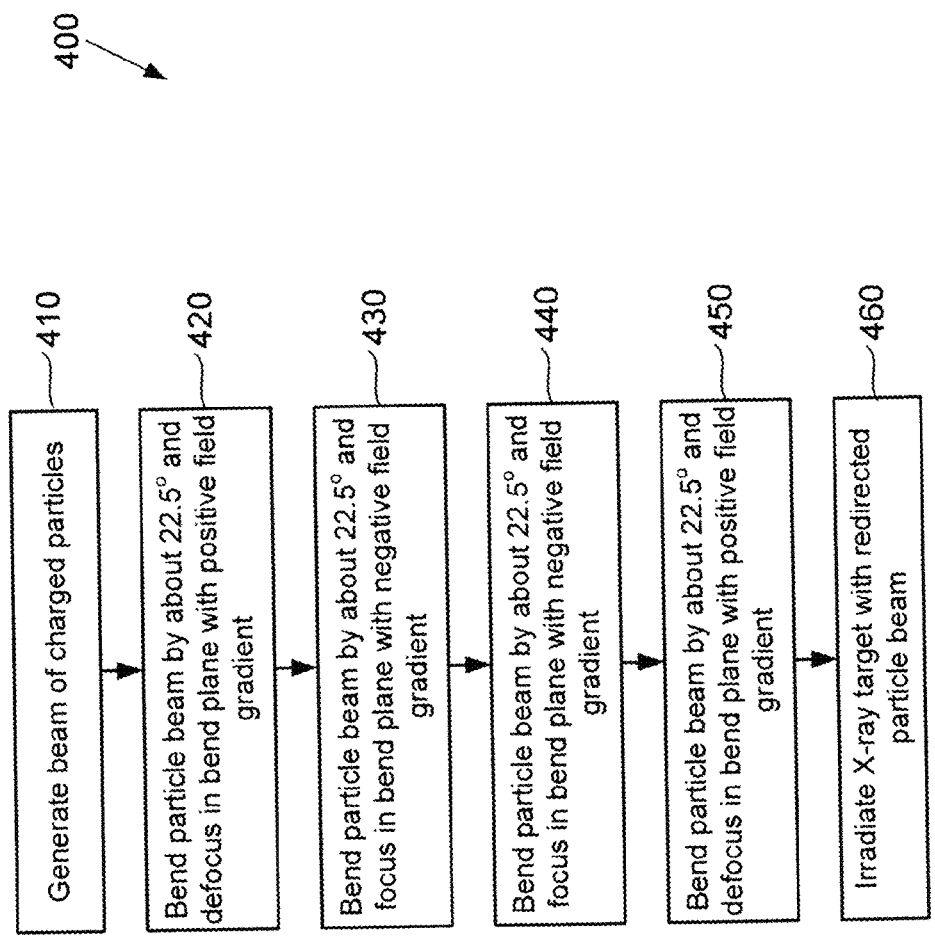
FIG. 4 is a flow chart of steps in an exemplary method for achromatically bending an electron beam by about 90° during radiation treatment.

The system 210 illustrated in FIGS. 2A-2B may be used to bend a beam of charged particles by about 90° during radiation treatment, according to method 400 illustrated in FIG. 4. The skilled artisan will readily appreciate modifications that may be made to the method of FIG. 4 for use with other types of radiation treatment systems, such as the gantry-based system illustrated in FIG. 12 and described in greater detail below.

Referring to FIG. 4, a beam of charged particles is generated, using any suitable techniques known in the art (step 410). For example, LINAC 221 illustrated in FIG. 2A may be used to generate a beam of charged particles such as electrons or protons, or even heavier particles such as boron, carbon, or neon. The beam may have full or finite emittance and a finite energy spread.

Then, the particle beam is bent by about 22.5°, and defocused in the bend plane with a positive field gradient (step 420 of FIG. 4). For example, as illustrated in FIG. 2B, beam 20 may pass through first bending magnet 201, which imparts about a 22.5° bend to beam 20 and defocuses the beam. After passing through first bending magnet 201, beam 20 diverges in the bend plane and converges in the non-bend plane as it passes through the drift region of dimension D5 between magnets 201 and 202, as illustrated in FIGS. 3A-3B.

Then, the particle beam is bent by about 22.5°, and focused in the bend plane with a negative field gradient (step 430 of FIG. 4). The field gradient used in step 430 may have a larger magnitude than that used in step 420. As illustrated in FIG. 2B, beam 20 may pass through second bending magnet 202, which imparts about a 22.5° bend to beam 20 and focuses the beam. After passing through second bending magnet 202, beam 20 converges, reaches a waist in both the bend and non-bend planes at a mid-point of the drift region between the second and third magnets, and then diverges as it passes through the second half of the drift region of dimension D6 between magnets 202 and 203, as illustrated in FIG. 3A. Optionally, beam 20 also passes through aperture 230, which is positioned approximately at the midpoint between magnets 202 and 203, and which spatially filters off energy particles that stray by a predetermined distance in the bend plane from the desired path of beam 20, as illustrated in FIG. 2B. In one embodiment, to achieve a substantially round output beam 20', collimation is done before or after system 210 because in the bend plane, the beam size is determined by the energy spread in the drift regions between the bend magnets.

Then, the particle beam is again bent by about 22.5°, and focused in the bend plane with a negative field gradient (step 440 of FIG. 4). For example, as illustrated in FIG. 2B, beam 20 may pass through third bending magnet 203, which imparts about a 22.5° bend to beam 20 and focuses the beam.

After passing through third bending magnet 203, beam 20 is convergent in the bend plane and divergent in the non-bend plane as it passes through the drift region of dimension D7 between magnets 203 and 204, as illustrated in FIGS. 3A and 3B.

Then, the particle beam is again bent by about 22.5°, and defocused in the bend plane with a positive field gradient (step 450 of FIG. 4). For example, as illustrated in FIG. 2B, beam 20 may pass through fourth bending magnet 204, which imparts about a 22.5° bend to beam 20 and defocuses the beam in the bend plane. After passing through fourth bending magnet 204, beam 20 has been deflected by a total of about 90° and is approximately collimated, resulting in deflected beam 20' as illustrated in FIG. 2B.

Optionally, in embodiments where deflected beam 20' is an electron beam, the deflected beam then may be used to irradiate an X-ray target (step 460 of FIG. 4). For example, as illustrated in FIG. 2B, beam 20' may for example be an electron beam that impinges on X-ray target 250 and thus generates an X-ray beam. The X-rays thus generated may then be used for radiation therapy, e.g., using methods known in the art.

The construction of bending magnets 201, 202, 203, and 204 will now be discussed in greater detail with references to FIGS. 5-6.

Figure 5:
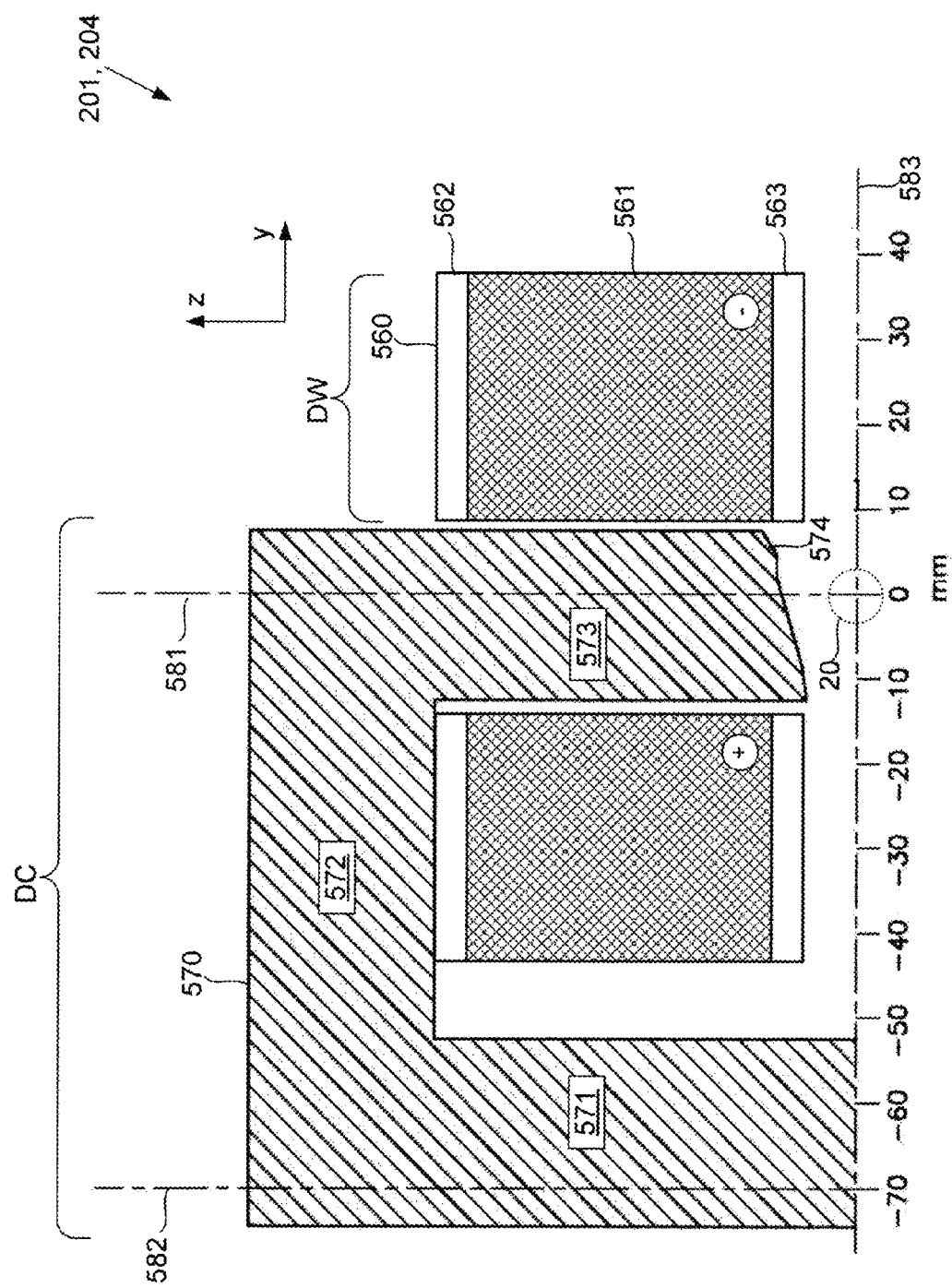
FIG. 5 schematically illustrates a cross-sectional view of an exemplary design for outer bending magnets (201, 204) for use in a system for achromatically bending an electron beam by about 90° during radiation treatment.

FIG. 5 schematically illustrates a cross-sectional view of outer bending magnets 201, 204, past which particle beam 20 travels. In some embodiments, the first and fourth bending magnets each may include an iron cored, dipole electromagnet having pole faces that are symmetrically disposed about the bend plane and are inclined relative to each other and shaped so as to generate a positive field gradient. A positive field gradient is such that the magnetic induction decreases with increasing distance from the approximate center of curvature. It should be understood that the first and fourth bending magnets 201, 204 may in some embodiments have substantially the same construction as one another. However, in some embodiments, fourth bending magnet 204 may be arranged as a "mirror image" of first bending magnet 201. The description below applies equally to both arrangements. In FIG. 5, axis 583 lies in the median plane of bending system 210, i.e., in the bend plane. An approximately cylindrical surface 581 has axis 582 as its approximate axis. The approximate center of curvature 220 of FIGS. 2B and 11 lies on this axis, at axis 583. The beam path travels along a curve defined by the intersection of the median plane and surface 581.

Outer bending magnets 201, 204 each include electromagnet 560 and core 570. Electromagnet 560 includes metal windings 561 and first and second cooling plates 562, 563 disposed above and below windings 561, which are configured to maintain windings 561 at a suitable temperature. Electromagnet 560 is substantially toroidal, with a preselected amount of current passing through windings 561 in the direction denoted by "+" and "−." Windings 560 have a thickness DW. Note that this method of coil (winding) construction is only one of several that may be used. Other suitable constructions include wire wound, air cooled and hollow conductor with cooling water channeled through the hollow conductor. In either of these cases, there are no "cooling plates." The specific winding technology may be determined by the specific parameters of the system, as well as practical considerations. In one illustrative embodiment, windings 561 are hollow copper conductor.

Core 570 is formed of a ferromagnetic material such as iron, has an overall thickness DC, and includes three portions 571, 572, 573. First core portion 571 is disposed outside of electromagnet 560; second core portion 572 is disposed over electromagnet 560; and third core portion 573 is disposed inside of the toroid defined by electromagnet 560. The lower surface 574 of the third core portion 573 is disposed at a spaced distance from particle beam path 20, and is shaped so as to generate a magnetic field gradient effective to bend the charged particles traveling along that path by a desired angle, in one embodiment about 22.5°. Specifically, shaped lower surface 574 is inclined relative to the median plane, shaped so as to enhance the strength of the magnetic field to the left of axis 481 relative to the field to the right of the axis, yielding a positive magnetic field index n and causing the charged particles to defocus in the bend plane. In one embodiment, shaped lower surface 574 is approximately hyperbolic.

Figure 6:
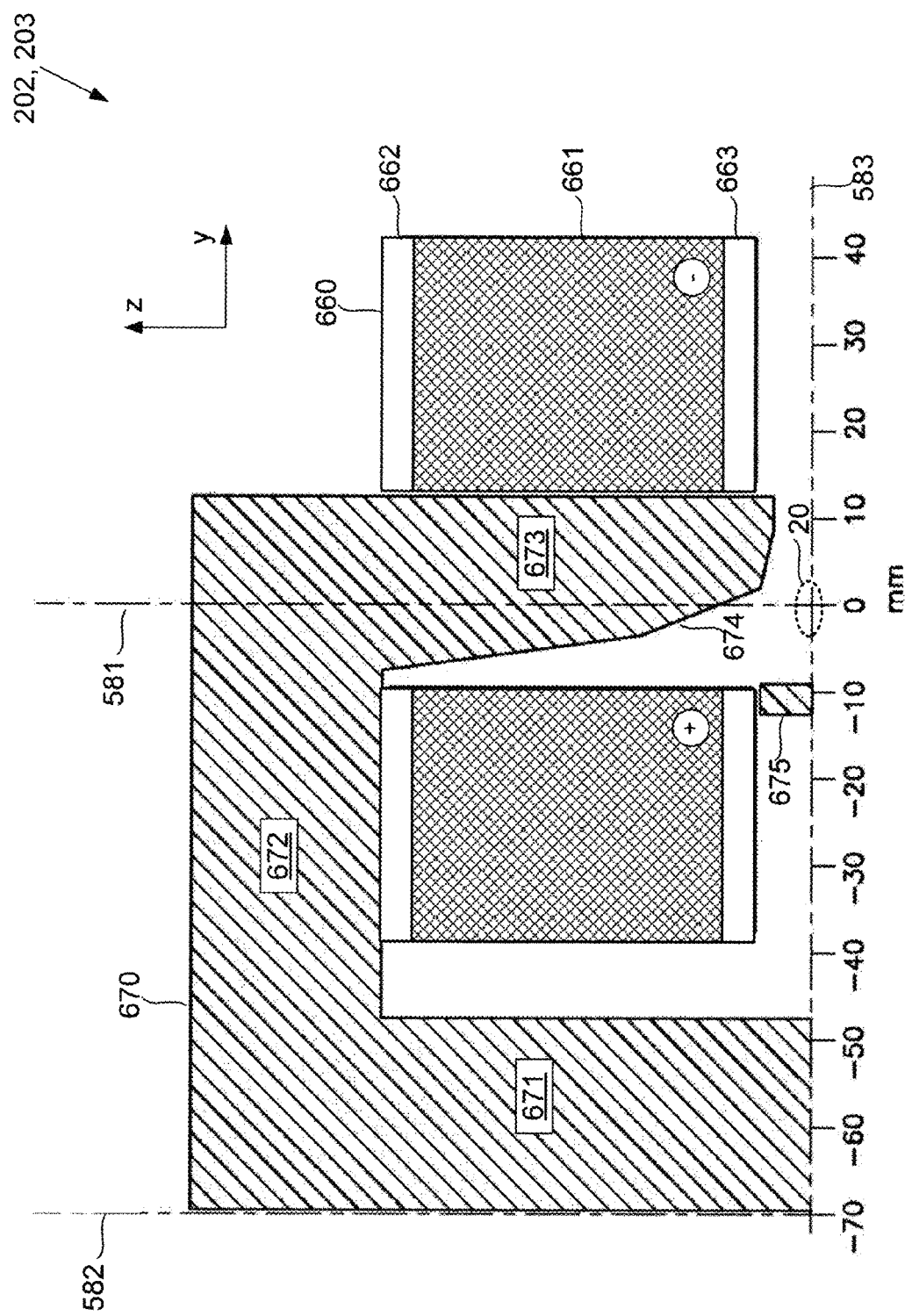
FIG. 6 schematically illustrates a cross-sectional view of an exemplary design for inner bending magnets (202, 203) for use in a system for achromatically bending an electron beam by about 90° during radiation treatment.

FIG. 6 schematically illustrates a cross-sectional view of inner bending magnets 202, 203 past which particle beam 20 travels. The second and third bending magnets each may include an iron cored, dipole electromagnet and having pole faces that are symmetrically disposed about the bend plane and are inclined relative to each other and shaped so as to generate a negative field gradient. A negative field gradient is such that the magnetic induction increases with increasing distance from the approximate center of curvature. It should be understood that the second and third bending magnets 202, 203 may in some embodiments have substantially the same construction as one another. However, in some embodiments, third bending magnet 203 may be arranged as a "mirror image" of second bending magnet 202. The description below applies equally to both arrangements. In FIG. 6, axis 583 lies in the median plane of bending system 210, i.e., the bend plane. An approximately cylindrical surface 581 has axis 582 as its approximate axis. The approximate center of curvature 220 of FIGS. 2B and 11 lie on this axis at axis 583. The beam path 20 travels along a curve defined by the intersection of the median plane and surface 581. Note that in FIG. 6, beam path 20 is illustrated as a horizontal ellipse, reflecting the beam convergence in the non-bend plane such as illustrated in FIG. 3B.

Inner bending magnets 202, 203 each include electromagnet 660 and core 670, which may have dimensions DW and DC as set forth above. Electromagnet 660 includes metal windings 661 and first and second cooling plates 662, 663 disposed above and below windings 661, which are configured to maintain windings 661 at a suitable temperature. Electromagnet 660 is substantially toroidal, with a preselected amount of current passing through windings 661 in the direction denoted by "+" and "−."

Core 670 is formed of a ferromagnetic material such as iron, and includes four portions 671, 672, 673, and 675. First core portion 671 is disposed outside of electromagnet 660; second core portion 672 is disposed over electromagnet 560; third core portion 673 is disposed inside of the toroid defined by electromagnet 560; and fourth core portion 675 is disposed beneath electromagnet 560. The lower surface 674 of the third core portion 673 is disposed at a spaced distance from particle beam path 20, and is shaped so as to generate a magnetic field gradient effective to bend the charged particles traveling along that path by about 22.5°. Specifically, shaped lower surface 674 is declined relative to the median plane 583 and shaped so as to enhance the strength of the magnetic field to the right of axis 581 relative to the field to the left of the axis, yielding a negative magnetic field index n and causing the charged particles to focus in the bend plane. In one embodiment, shaped lower surface 674 is approximately hyperbolic. The decline of shaped lower surface 674 illustrated in FIG. 6 may also be seen to be significantly greater than the incline of shaped lower surface 574 illustrated in FIG. 5, thus yielding a greater field index n.

It should be understood that the dimensions and materials used in the inner and outer bending magnets, as well as the shape of lower surfaces 574, 674, may be modified based on the particular type and energy of charged particles to be bent, as well as the desired angle through which the particles are to be bent and the amount of focusing desired in the bend and non-bend planes. Exemplary dimensions and parameters of the outer and inner bending magnets illustrated in FIGS. 5-6, as configured for use with electrons of energy 10 MeV, are set forth below in Table 2.

TABLE 2

| Dimension/Parameter | Outer Magnets (201, 204) | Inner Magnets (202, 203) |
| --- | --- | --- |
| DW | 30 mm | 30 mm |
| DW/D3 | 0.04286 | 0.04286 |
| DC | 82 mm | 82 mm |
| Winding Current | 4000 A | 4000 A |
| B-Field at Origin (0,0) | 5199.5 Gauss | 5635.5 Gauss |
| $B_o$ | 0.5 Tesla | 0.5 Tesla |
| Field Index n at Origin (0,0) | +2.357 | −6.801 |

The performance characteristics of inner and outer bending magnets configured as illustrated in FIGS. 5-6 and having the dimensions and parameters set forth in Table 2 were modeled using two-dimensional POISSON modeling for an electron beam 20 of energy 10 MeV, the results of which are set forth in FIGS. 7-10.

Figure 7:
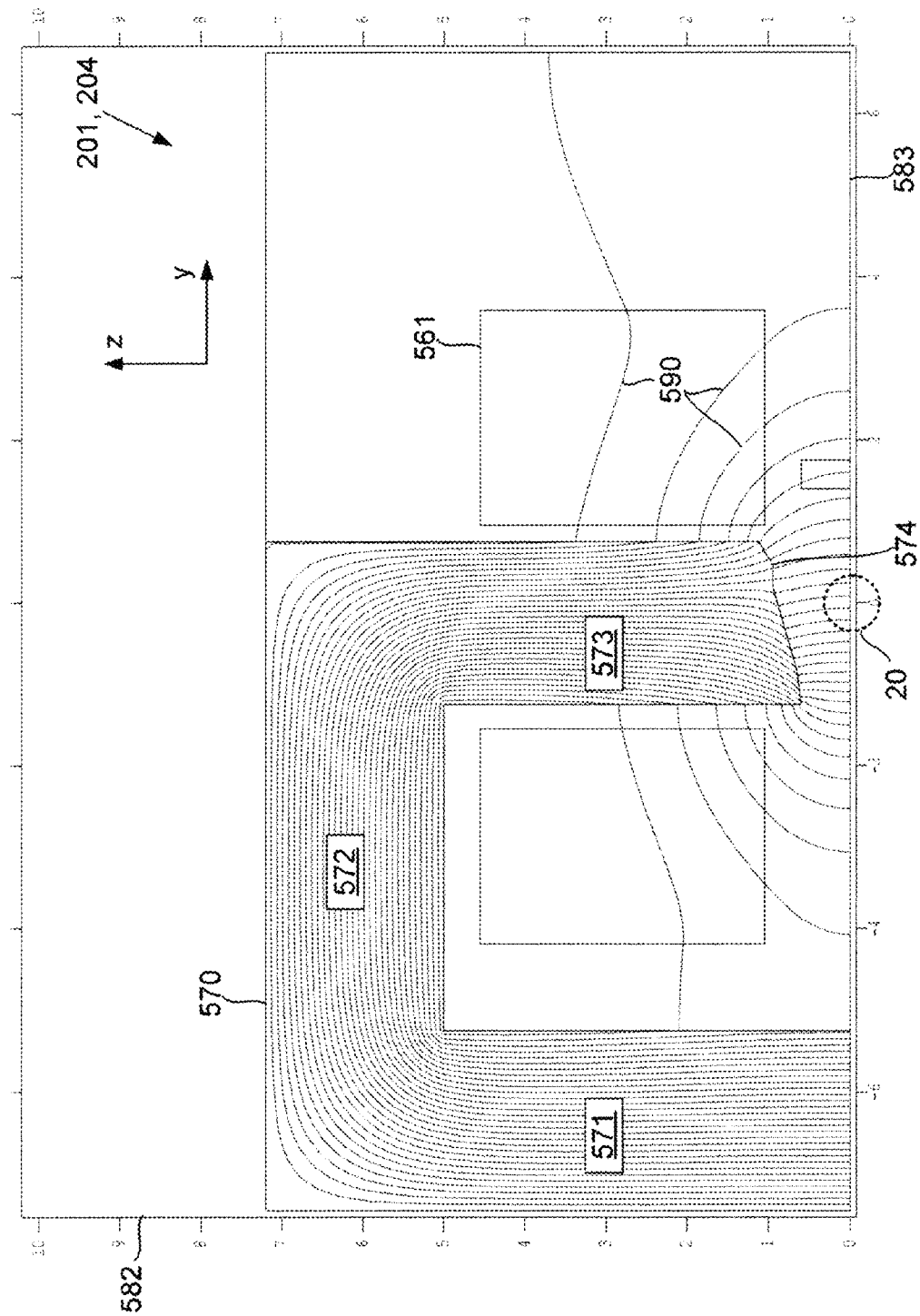
FIG. 7 is a magnetic flux plot of a POISSON two-dimensional model of the outer bending magnets (201, 204) of FIG. 5.
Figure 8:
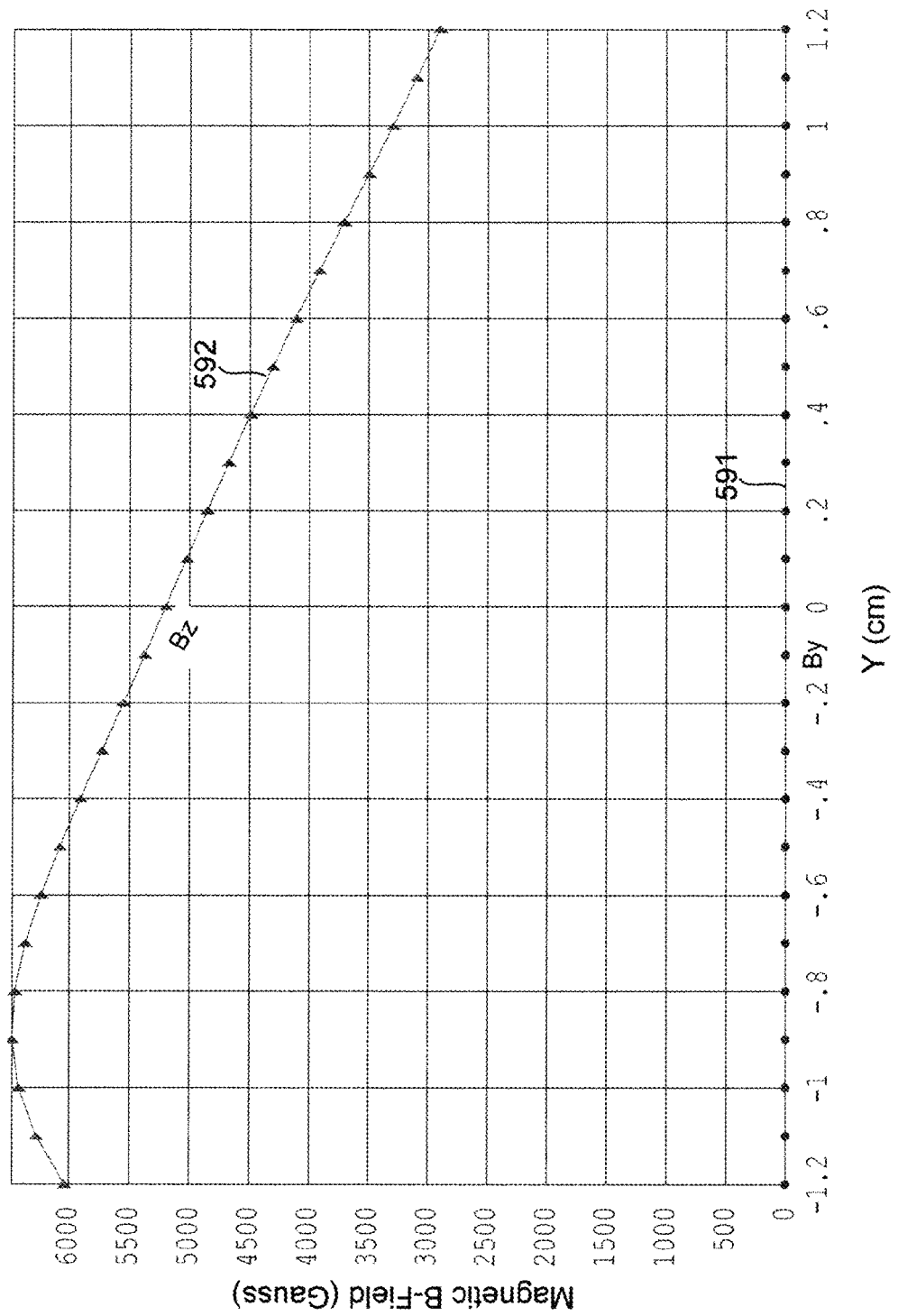
FIG. 8 is a plot of magnetic field components versus transverse position from the POISSON two-dimensional model of the outer bending magnets (201, 204) of FIG. 7.

Specifically, FIG. 7 is a magnetic flux plot of a POISSON two-dimensional model of outer bending magnets 201, 204, in which the magnetic field lines are denoted 590. FIG. 8 is a plot of the y-direction magnetic field component 591 and the z-direction magnetic field 592 component versus transverse position near the origin (0,0), e.g., near beam path 20, from the model of FIG. 7. As can be seen in FIG. 8, the y-direction magnetic field component 591 is substantially zero in this region, while the z-direction magnetic field component 591 varies smoothly and increases from right to left, with an inflection point around −0.8 cm.

Figure 9:
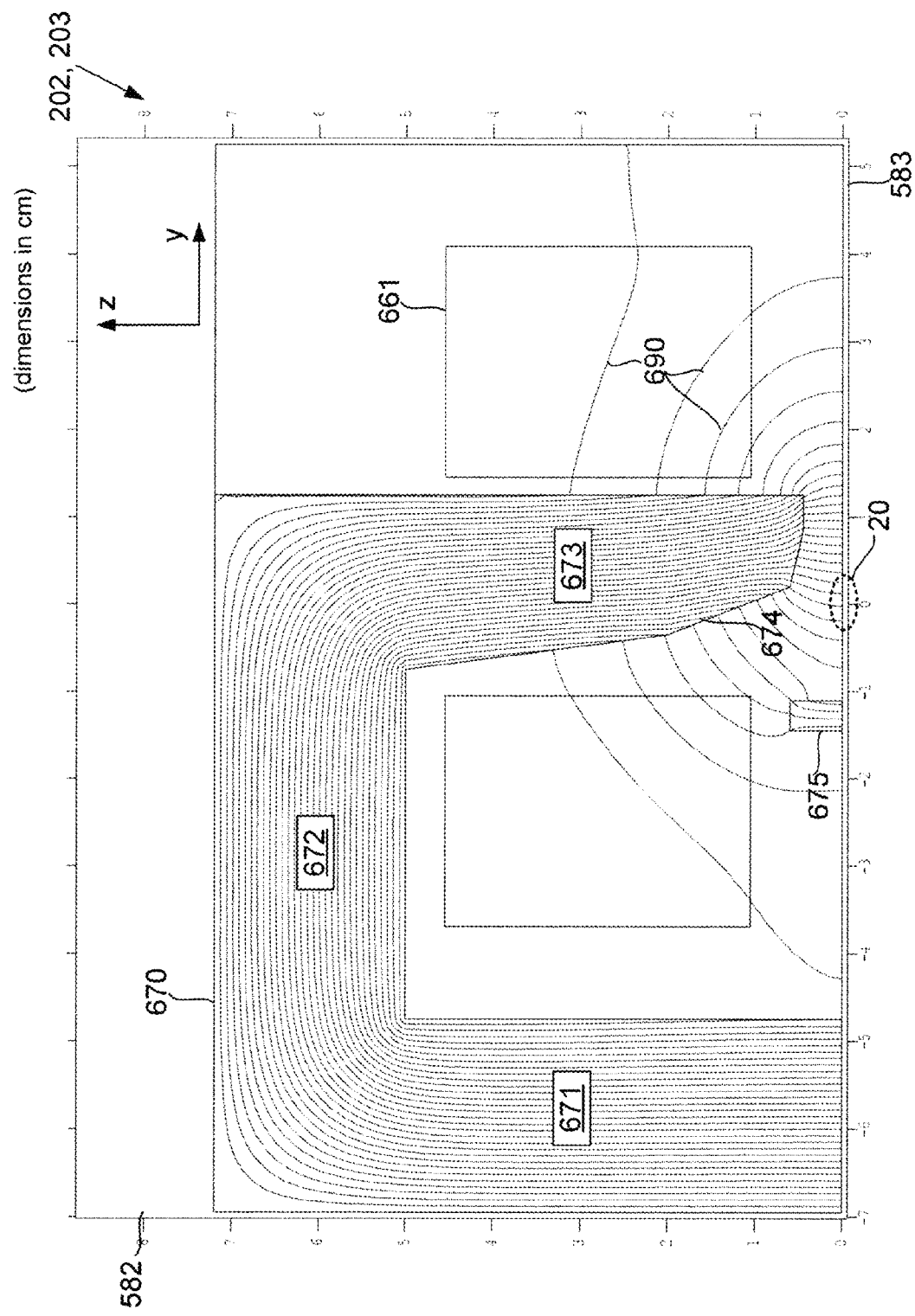
FIG. 9 is a magnetic flux plot of a POISSON two-dimensional model of the inner bending magnets (202, 203) of FIG. 6.
Figure 10A:
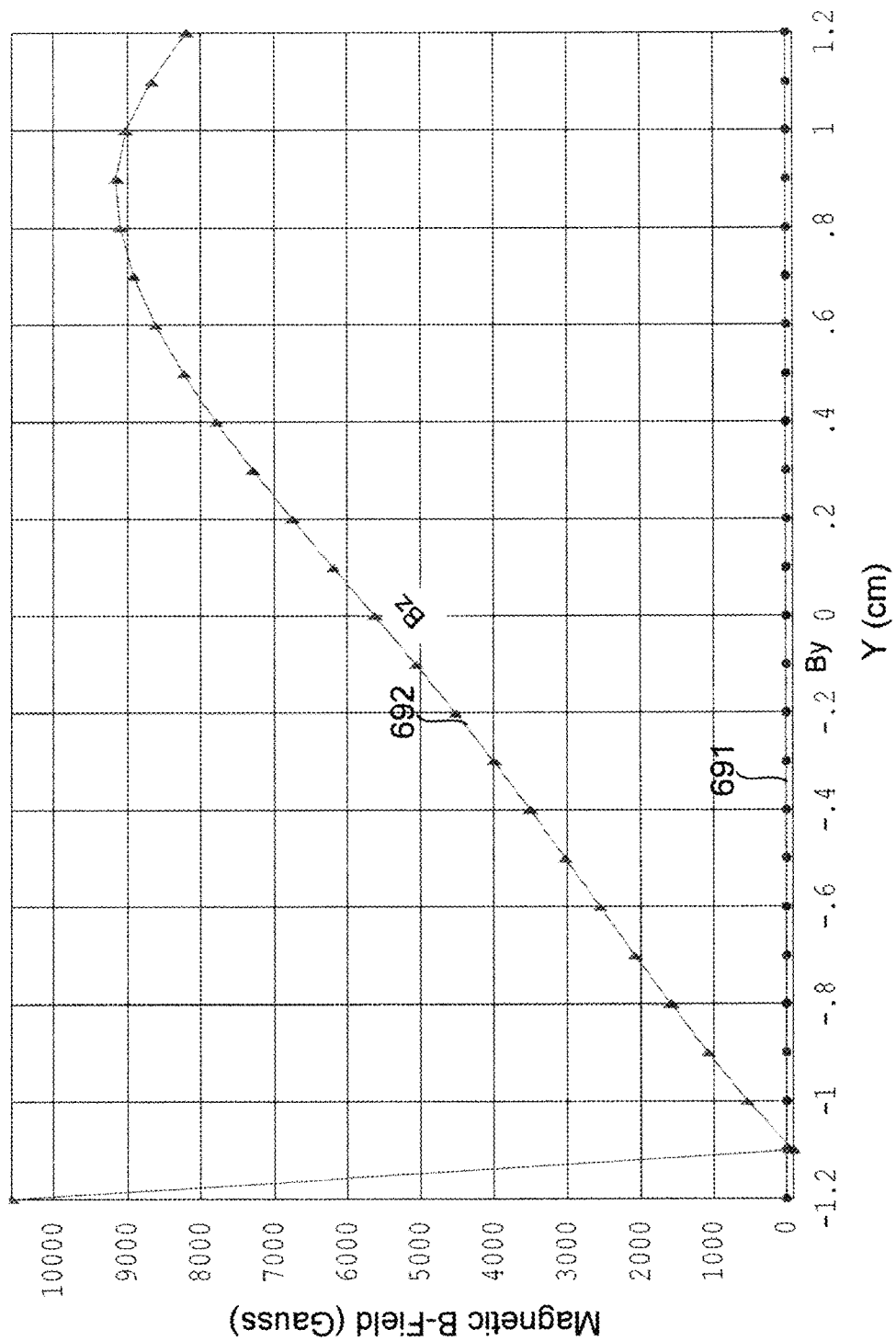
FIG. 10A is a plot of magnetic field components versus transverse position from the POISSON two-dimensional model of the inner bending magnets (202, 203) of FIG. 9.

FIG. 9 is a magnetic flux plot of a POISSON two-dimensional model of inner bending magnets 202, 203, in which the magnetic field lines are denoted 690. FIG. 10A is a plot of the y-direction magnetic field component 691 and the z-direction magnetic field component 692 versus transverse position near the origin (0,0), e.g., near beam path 20, from the model of FIG. 9. As can be seen in FIG. 10A, the y-direction magnetic field component 691 is substantially zero in this region, while the z-direction magnetic field component 691 varies smoothly and declines from right to left, with an inflection point around +0.8 cm. Although the magnitude of the z-component of the magnetic fields near the origin is relatively similar in FIGS. 8 and 10A (e.g., approximately 5200 Gauss and 5630 Gauss, respectively), it can be seen that the magnetic field gradient n in the z-direction i.e., the slope of the z-direction magnetic field component, is significantly greater for the inner bending magnets and of opposite sign, as shown in FIG. 10A, as compared to that for the outer bending magnets, as shown in FIG. 8.

In some embodiments, the pole faces are shaped so as to introduce higher-order magnetic field components so as to control geometric and chromatic aberrations in the beam which may be produced by the simple linear field gradients heretofore described. That is, system 210 illustrated in FIGS. 2A-2B also may be achromatic to second order, or to even higher orders. Such second order achromaticity may be useful, in facilitating substantially uniform bending of particle beams in which the particles have energies that vary about a central energy value, e.g., by about 10% above and below a central energy value, or even by about 15% above and below a central energy value.

Figure 10B:
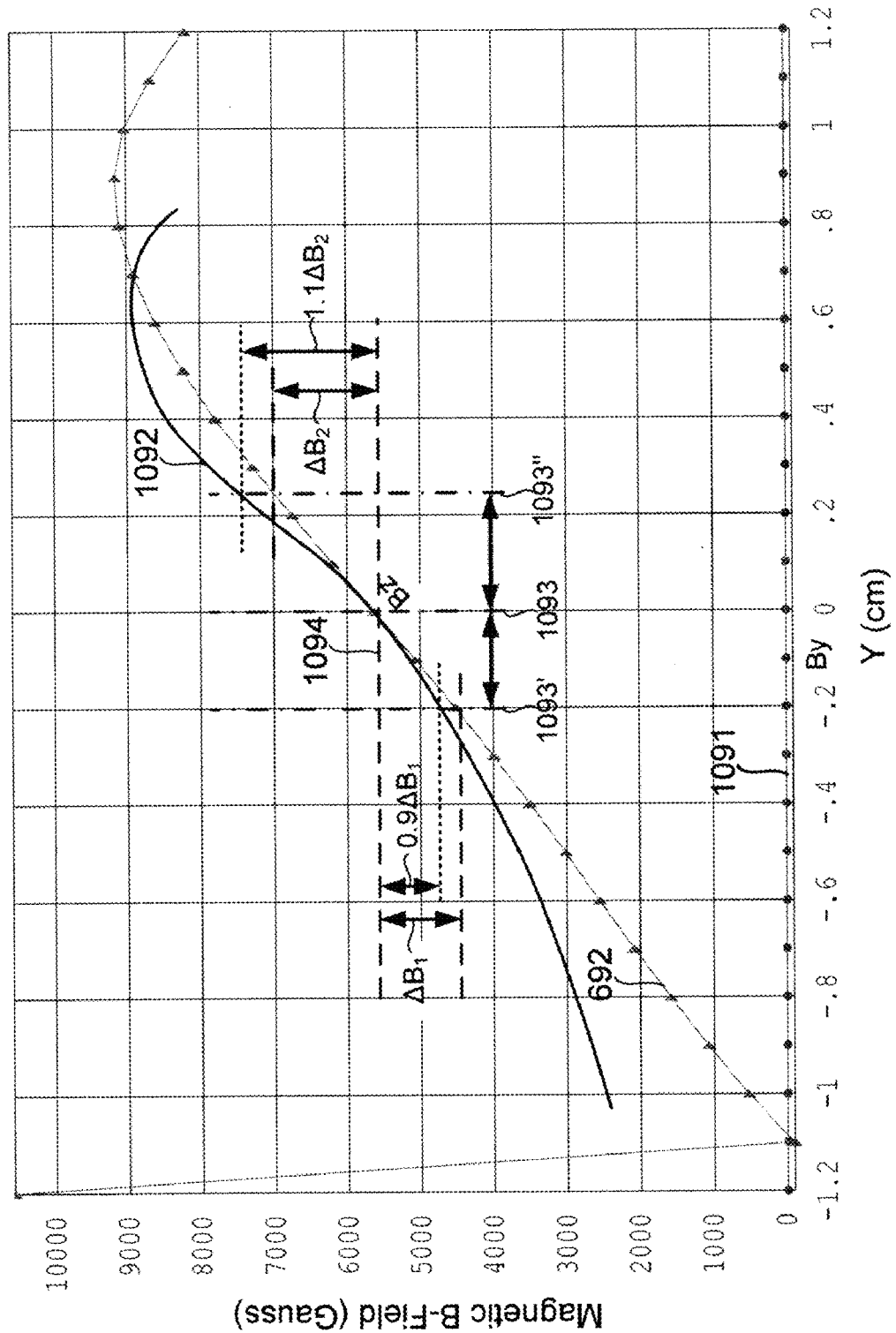
FIG. 10B is a plot of magnetic field components versus transverse position that also include higher-order magnetic gradient terms relative to those shown in FIG. 10A.

FIG. 10B is a plot of the x-direction magnetic field component 1091 and the z-direction magnetic field component 1092 versus transverse position near the origin (0,0), e.g., near beam path 20, for a model similar to that illustrated in FIG. 9 but configured so as to introduce second-order terms into the z-direction magnetic field component 1092. The z-direction magnetic field component 692 from FIG. 10A, which lacks such second-order terms, is also shown for comparison. In the example illustrated in FIG. 10B, the particle beam has an energy spread of plus or minus 10% about a central energy value 1093, the lower end of this spread designated 1093' and the upper end of this spread designated 1093". Absent the second-order terms included in z-direction magnetic field component 1092, particles having energies at the lower end 1093' of the energy spread may deviate from beam path 20 as a result of overfocusing by the inner magnets 202, 203, caused by field strength greater than that needed to bend those particles by the same amount as are particles closer to the central energy value 1093. Similarly, particles having energies at the upper end 1093" of the energy spread may deviate from beam path 20 as a result of underfocusing by the inner magnets 202, 203, caused by too low a field strength to bend those particles by the same amount as are particles closer to the central energy value 1093.

In some embodiments, the second-order curve 1092 illustrated in FIG. 10B compensates for these bending errors by configuring inner bending magnets 202, 203 so as to generate a z-direction magnetic field component that quadratically curves upwards on either side of the central energy value 1093. Specifically, particles having energies at the lower end 1093' of the energy spread experience a magnetic field that is decreased from $\Delta B_1$ to $0.9\Delta B_1$, while particles having energies at the upper end 1093" of the energy spread experience a magnetic field that is increased from $\Delta B_2$ to $1.1\Delta B_2$. Note that such a curved profile does not distort the image of a monochromatic full emittance beam such as illustrated in FIG. 3D, because the beam crosses over between inner magnets 202, 203, and as a result electrons that are overfocused at magnet 202 may be underfocused at magnet 203, and electrons that are underfocused at magnet 202 may be overfocused at magnet 203, resulting in cancellation of the effect.

Second order magnetic field terms such as illustrated in FIG. 10B may be achieved, for example, by adding an appropriate second order term to the gradients generated by the inner (second and third) bending magnets, for example by finely adjusting the shape of pole face 674 so as to generate second order field gradients. In one exemplary embodiment, fourth core portion 675 of inner bending magnets 202, 203, illustrated in FIG. 6, is removed or changed in position relative to that shown so as to generate higher order achromaticity. The particular shape of second-order curve 1092 is merely exemplary, and any number of magnets 201-204 may be configured to introduce any suitable higher-order terms into the magnetic fields to which particle beam 20 is exposed. In one illustrative embodiment, the z-component of the magnetic field generated by the inner magnets 202, 203 has a substantially quadratic profile over a location corresponding to the energy spread of the particles, e.g., over a 20% full width energy range, or even over a 30% full width energy range.

Note that although gradient magnets having shaped pole faces 574, 674 are illustrated in FIGS. 5-6, other types of magnets may be used to achieve a similar effect, e.g., to each achromatically bend charged particles by a desired angle, in one embodiment by about 22.5°, resulting in a net bend angle of about 90°. For example, quadrupole magnets may be appropriately configured to provide comparable magnetic fields and field gradients to those shown in FIGS. 7-10, and performance comparable to that shown in FIGS. 3A-3D.

In one illustrative embodiment, magnets 201-204 illustrated in FIG. 2B are rectangular, laminated electromagnets having pole faces respectively shaped as illustrated in FIGS. 5-6. As is known in the art, the core of an electromagnet may be laminated, e.g., using thin sheets of iron, to impede the circulation of induced currents that would otherwise resist rapid changes in magnetic field. As such, the use of laminated cores in magnets 201-204 may allow the fields generated by those magnets to be changed relatively quickly, for example on the millisecond timescale, for example to bend particle beams of different energies in quick succession. Alternatively, magnets 201-204 are rectangular, but are not laminated.

Figure 11:
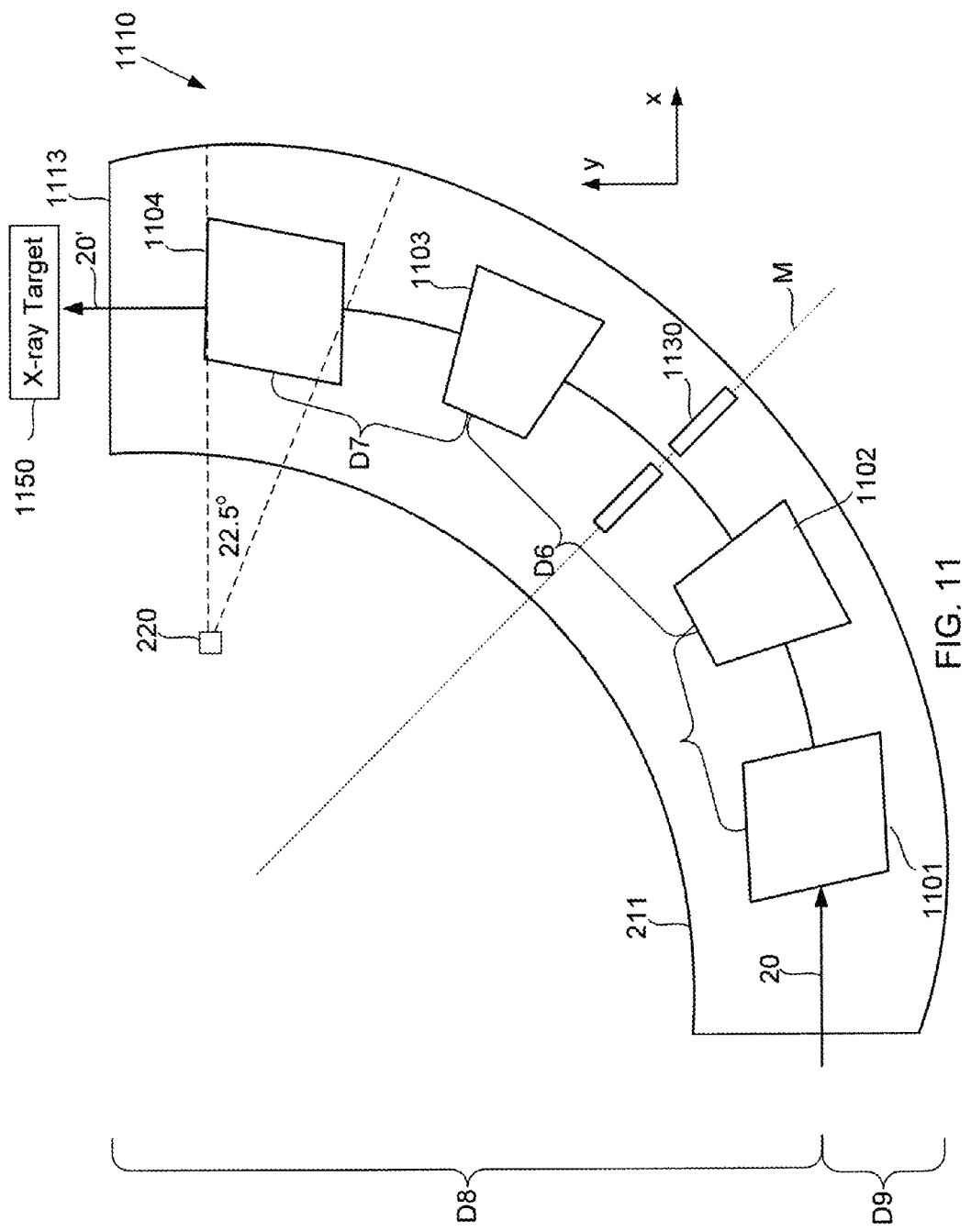
FIG. 11 schematically illustrates a plan view of an alternative achromatic bending system.

In an alternative embodiment, illustrated in FIG. 11, non-rectangular first, second, third, and fourth magnets 1101-1104 may be used in alternative beam bending system 1100. These magnets may be laminated, as described above, or alternatively may be non-laminated. As illustrated in FIG. 11, outer (first and fourth) magnets are shaped as parallelograms, and inner (second and third) magnets are shaped as trapezoids. Such shaped magnets may be referred to as "wedge" magnets.

Figure 12:
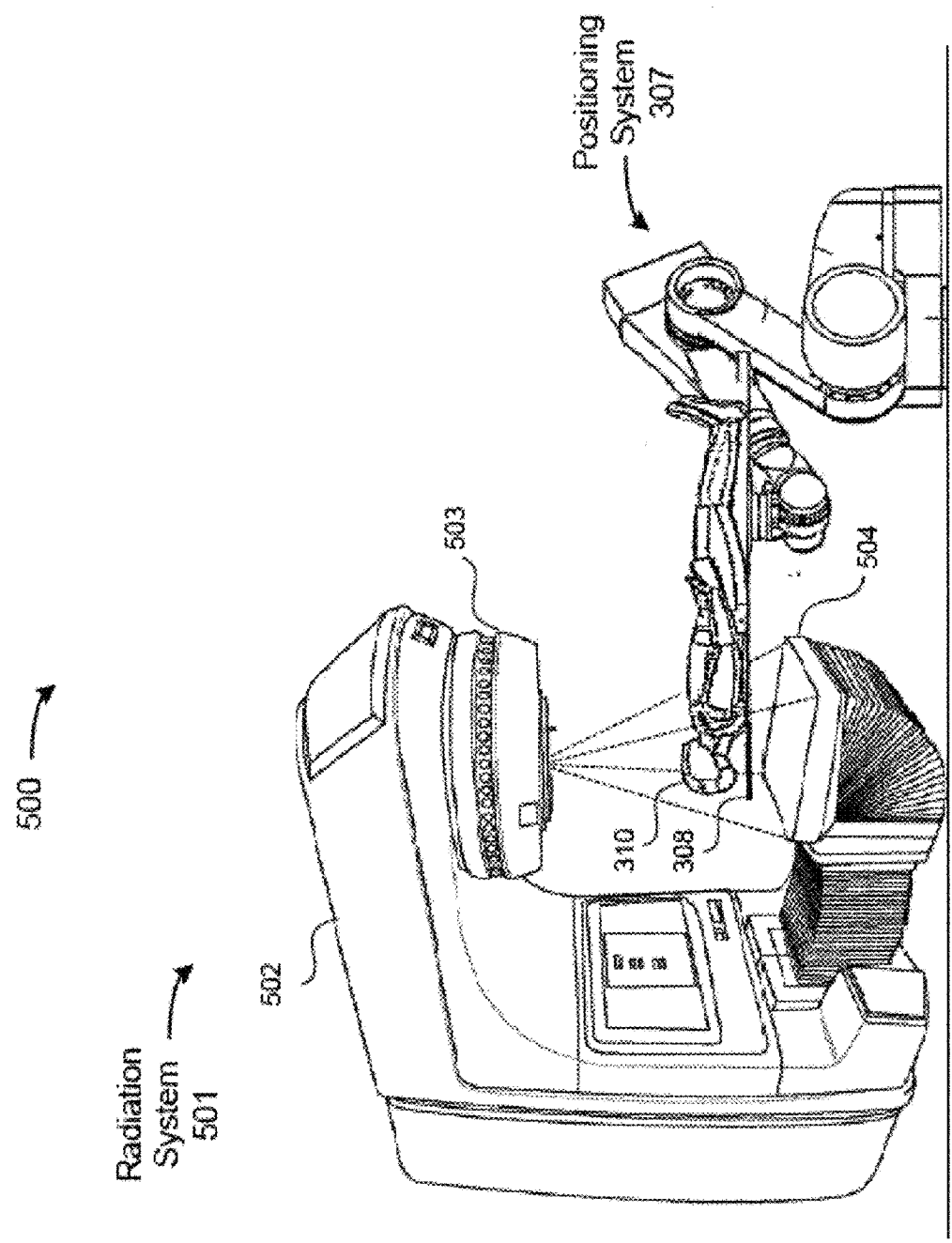
FIG. 12 schematically illustrates a perspective view of a gantry-based radiation treatment system having a system for achromatically bending an electron beam by about 90° during radiation treatment.

As noted above, the systems and methods of the present invention are also compatible with radiation treatment systems other than the robot-based system 100 illustrated in FIG. 1. For example, FIG. 12 schematically illustrates a gantry-based system 500. System 500 includes patient positioning system 307 and gantry-based radiation system 501. Gantry-based radiation system 501 includes a gantry 502, a LINAC 503, and a portal imaging device 504. LINAC 503 is arranged substantially horizontally, and is coupled to a 90° achromatic bending system such as described herein (not illustrated in FIG. 12). Gantry 502 is configured to move LINAC 503 in a fixed plane about the patient 310. LINAC 503 may include a multi-leaf collimator. Patient positioning system 307 may be a robotic system for moving patient 310 relative to the gantry 502, as shown, or any other suitable patient support system as known to the skilled artisan. Gantry-based radiation system 510 and patient positioning system 307 are in operable communication with a controller (not shown) configured for operation with the particular radiation system and patient positioning system being used.

While various illustrative embodiments of the invention are described above, it will be apparent to one skilled in the art that various changes and modifications may be made therein without departing from the invention. For example, although approximately 90° bends have predominantly been described, bends of other angles also may be made by suitably modifying the systems and methods described herein. The appended claims are intended to cover all such changes and modifications that fall within the true spirit and scope of the invention.

What is claimed:

1. A system for achromatically bending a particle beam by about 90°, the system comprising:
   first, second, third, and fourth bending magnets serially arranged along a beam path of the particle beam,
   the first and fourth bending magnets being configured to generate a positive field gradient that defocuses the particle beam in a bend plane;

the second and third bending magnets being configured to generate a negative field gradient that focuses the particle beam in the bend plane;

the first, second, third, and fourth bending magnets collectively bending the particle beam by about 90°.

2. The system of claim 1, wherein the first, second, third, and fourth bending magnets each bend the particle beam by about 22.5°.

3. The system of claim 1, wherein the first and fourth bending magnets each comprise an iron cored, dipole electromagnet having pole faces that are inclined relative to one another and shaped so as to generate the positive field gradient, and wherein the second and third bending magnets each comprise an iron cored, dipole electromagnet having pole faces that are inclined relative to one another and shaped so as to generate the negative field gradient.

4. The system of claim 3, wherein the pole faces of the first, second, third, and fourth bending magnets are shaped such that the positive field gradient is substantially weaker than the negative field gradient.

5. The system of claim 3, wherein the pole faces of the first, second, third, and fourth bending magnets are each approximately hyperbolically shaped.

6. The system of claim 1, wherein the second bending magnet focuses the particle beam to a beam waist located reflection mirror plane midway between the second and third bending magnets.

7. The system of claim 1, further comprising an X-ray target configured to be irradiated with the bent particle beam.

8. The system of claim 1, wherein a midpoint between the second and third bending magnets defines a mirror plane, the first and fourth bending magnets being positioned substantially symmetrically across the mirror plane from one another, and the second and third bending magnets being positioned substantially symmetrically across the mirror plane from one another.

9. The system of claim 1, wherein the particle beam has a substantially round profile before entering the system and following bending.

10. The system of claim 1, wherein the particle beam comprises particles having an energy spread of 30% full width or less.

11. A method for achromatically bending a particle beam by about 90°, the system comprising:

bending the particle beam with a first bending magnet that defocuses the particle beam in a first plane with a positive field gradient, and then bending the particle beam with a second bending magnet that focuses the particle beam in the first plane with a negative field gradient, and then bending the particle beam with a third bending magnet that focuses the particle beam in the first plane with a negative field gradient, and then bending the particle beam with a fourth bending magnet that defocuses the particle beam in the first plane with a positive field gradient, wherein the first, second, third, and fourth bending magnets collectively bend the particle beam by about 90°.

12. The method of claim 11, wherein the first, second, third, and fourth bending magnets are serially arranged along a beam path of the particle beam, and wherein a midpoint between the second and third bending magnets defines a reflection plane, the first and fourth bending magnets being positioned substantially symmetrically across the reflection plane from one another, and the second and third bending magnets being positioned substantially symmetrically across the reflection plane from one another.

13. The method of claim 11, wherein the positive field gradient is substantially weaker than the negative field gradient.

14. The method of claim 11, wherein the first and fourth bending magnets each comprise an electromagnet and a core having a pole face that is inclined relative to a second plane and shaped so as to generate the positive field gradient, and wherein the second and third bending magnets each comprise an electromagnet and a core having a pole face that is declined relative to the second plane and shaped so as to generate the negative field gradient.

15. The method of claim 14, wherein the pole faces of the first, second, third, and fourth bending magnets are each approximately hyperbolically shaped.

16. The method of claim 11, wherein the first, second, third, and fourth bending magnets each bend the particle beam by about 22.5°.

17. The method of claim 11, wherein the second bending magnet focuses the particle beam to a beam waist located at the reflection plane.

18. The method of claim 11, wherein the particle beam has a substantially round profile before entering the system and has a substantially round profile following bending.

19. The method of claim 11, wherein the particle beam comprises particles having an energy spread of 30% full width or less.

20. A system for achromatically bending a particle beam by about 90°, the system comprising:

first, second, third, and fourth bending magnets serially arranged along a beam path of the particle beam, a midpoint between the second and third bending magnets defining a reflection plane, the first and fourth bending magnets being positioned substantially symmetrically across the reflection plane from one another, and the second and third bending magnets being positioned substantially symmetrically across the reflection plane from one another;

the first and fourth bending magnets being configured to generate a positive field gradient that defocuses the particle beam in a bend plane; and the second and third bending magnets being configured to generate a negative field gradient that focuses the particle beam in the bend plane.

* * * * *